(12) United States Patent
Mayer et al.

(10) Patent No.: US 10,966,728 B2
(45) Date of Patent: Apr. 6, 2021

(54) MEDICAL DEVICE FOR TREATING VASCULAR MALFORMATIONS

(71) Applicant: ENDOSTREAM MEDICAL LTD., Tel Aviv (IL)

(72) Inventors: Danel Mayer, Ramat Hasharon (IL); Alon May, Caesarea (IL); Yuval Shezifi, Haifa (IL)

(73) Assignee: ENDOSTREAM MEDICAL LTD., Tel Aviv (IL)

( * ) Notice: Subject to any disclaimer, the term of this patent is extended or adjusted under 35 U.S.C. 154(b) by 194 days.

(21) Appl. No.: 16/311,744

(22) PCT Filed: Jun. 21, 2017

(86) PCT No.: PCT/IL2017/050694
§ 371 (c)(1),
(2) Date: Dec. 20, 2018

(87) PCT Pub. No.: WO2017/221252
PCT Pub. Date: Dec. 28, 2017

(65) Prior Publication Data
US 2019/0209181 A1    Jul. 11, 2019

Related U.S. Application Data

(60) Provisional application No. 62/444,963, filed on Jan. 11, 2017, provisional application No. 62/352,578, filed on Jun. 21, 2016.

(51) Int. Cl.
*A61B 17/12* (2006.01)
*A61B 90/00* (2016.01)
*A61B 17/00* (2006.01)

(52) U.S. Cl.
CPC .... *A61B 17/12145* (2013.01); *A61B 17/1204* (2013.01); *A61B 17/12113* (2013.01);
(Continued)

(58) Field of Classification Search
CPC .......... A61B 17/12145; A61B 17/1204; A61B 17/12113
See application file for complete search history.

(56) References Cited

U.S. PATENT DOCUMENTS 5,350,397 A    9/1994 Palermo et al.
5,649,949 A    7/1997 Wallace et al.
(Continued)

FOREIGN PATENT DOCUMENTS

CN    202136073    2/2012
CN    203787320    8/2014
(Continued)

OTHER PUBLICATIONS

Nit-Occlud PDA, pfm medical (Jun. 2012).
(Continued)

*Primary Examiner* — Richard G Louis
(74) *Attorney, Agent, or Firm* — Sughrue Mion, PLLC

(57) ABSTRACT

A non-occlusive device is provided that includes a coilable section and a docking section. The coilable section is configured to become coiled into a coil when deployed from a microcatheter within a vascular malformation. The coil is shaped so as to define a sequence of concentric loops. The coil is configured to bridge a neck of the vascular malformation so as to at least partially cover an orifice of the vascular malformation, when in use. The docking section is configured to be deployed from the microcatheter within the vascular malformation. The docking section is configured to, when in use, perform one or more functions selected from the group consisting of: anchoring the device within the vascular malformation, stabilizing the device within the vascular malformation, assisting with positioning of the device within the vascular malformation, and intertwining
(Continued)

detachable coils delivered to the vascular malformation. Other embodiments are also described.

21 Claims, 10 Drawing Sheets

(52) U.S. Cl.
CPC ..... *A61B 17/1215* (2013.01); *A61B 17/12118* (2013.01); *A61B 2017/00526* (2013.01); *A61B 2017/00867* (2013.01); *A61B 2017/1205* (2013.01); *A61B 2090/3966* (2016.02)

(56) References Cited

U.S. PATENT DOCUMENTS

| | | | |
|---|---|---|---|
| 5,749,891 A | 5/1998 | Ken et al. | |
| 5,935,148 A | 8/1999 | Villar et al. | |
| 6,036,720 A | 3/2000 | Abrams et al. | |
| 6,306,141 B1 | 10/2001 | Jervis | |
| 6,338,736 B1 | 1/2002 | Boosfeld et al. | |
| 6,371,972 B1 | 4/2002 | Wallace et al. | |
| 6,383,174 B1 | 5/2002 | Eder | |
| 6,506,204 B2 | 1/2003 | Mazzocchi | |
| 6,551,305 B2 | 4/2003 | Ferrera et al. | |
| 6,740,096 B2 | 5/2004 | Teague et al. | |
| 6,790,218 B2 | 9/2004 | Jayaraman | |
| 7,128,736 B1 | 10/2006 | Abrams et al. | |
| 7,229,461 B2 | 6/2007 | Chin et al. | |
| 7,323,000 B2 | 1/2008 | Monstdt et al. | |
| 7,377,932 B2 | 5/2008 | Mitelberg et al. | |
| 7,569,066 B2 | 8/2009 | Gerberding et al. | |
| 8,007,509 B2 | 8/2011 | Buiser et al. | |
| 8,333,796 B2 | 12/2012 | Tompkins et al. | |
| 8,444,667 B2 | 5/2013 | Porter | |
| 8,518,064 B2 | 8/2013 | Kurrus et al. | |
| 8,570,343 B2 | 10/2013 | Halstead | |
| 8,747,454 B2 | 6/2014 | Khairkhahan et al. | |
| 8,764,772 B2 | 7/2014 | Tekulve | |
| 8,906,057 B2 | 12/2014 | Connor et al. | |
| 9,138,232 B2 | 9/2015 | Connor | |
| 9,629,635 B2 | 4/2017 | Hewitt et al. | |
| 2002/0049468 A1 | 4/2002 | Streeter et al. | |
| 2002/0107534 A1 | 8/2002 | Schaefer et al. | |
| 2002/0169473 A1 | 11/2002 | Sepetka et al. | |
| 2003/0055451 A1* | 3/2003 | Jones | A61B 17/12172 606/200 |
| 2003/0216772 A1 | 11/2003 | Konya et al. | |
| 2004/0034386 A1* | 2/2004 | Fulton | A61F 2/91 606/200 |
| 2004/0098027 A1 | 5/2004 | Teoh et al. | |
| 2004/0167597 A1 | 8/2004 | Costantino et al. | |
| 2005/0038460 A1 | 2/2005 | Jayaraman | |
| 2005/0107823 A1 | 5/2005 | Leone et al. | |
| 2005/0187564 A1* | 8/2005 | Jayaraman | A61B 17/12022 606/141 |
| 2006/0155323 A1 | 7/2006 | Porter et al. | |
| 2006/0206199 A1 | 9/2006 | Churchwell et al. | |
| 2007/0083230 A1* | 4/2007 | Javois | A61B 17/12172 606/213 |
| 2007/0123928 A1 | 5/2007 | Farnan | |
| 2007/0150045 A1 | 6/2007 | Ferrera | |
| 2008/0114436 A1 | 5/2008 | Dieck et al. | |
| 2008/0300616 A1 | 12/2008 | Que et al. | |
| 2009/0099647 A1 | 4/2009 | Glimsdale et al. | |
| 2009/0216265 A1 | 8/2009 | DeVries et al. | |
| 2010/0121350 A1 | 5/2010 | Mirigian | |
| 2011/0022149 A1 | 1/2011 | Cox et al. | |
| 2012/0071911 A1 | 3/2012 | Sadasivan et al. | |
| 2012/0143237 A1 | 6/2012 | Cam et al. | |
| 2014/0180377 A1 | 6/2014 | Bose et al. | |
| 2017/0135701 A1 | 5/2017 | Beckham et al. | |
| 2017/0150971 A1 | 6/2017 | Hines | |
| 2017/0333678 A1 | 11/2017 | Bowman et al. | |
| 2017/0367708 A1 | 12/2017 | Mayer et al. | |

FOREIGN PATENT DOCUMENTS

| | | |
|---|---|---|
| WO | 2012/158883 A1 | 11/2012 |
| WO | 2014/165256 | 10/2014 |
| WO | 2016/108241 | 7/2016 |

OTHER PUBLICATIONS

Medtronic EV3 Axium Youtube excerpts downloaded Aug. 13, 2018.
An International Search Report and a Written Opinion both dated Oct. 3, 2017, which issued during the prosecution of Applicant's PCT/IL2017/050694.
An International Search Report and a Written Opinion both dated Apr. 19, 2016, which issued during the prosecution of Applicant's PCT/IL2015/051271.
U.S. Appl. No. 62/352,578, filed Jun. 21, 2016.
U.S. Appl. No. 62/444,963, filed Jan. 11, 2017.
An Invitation to pay additional fees dated Mar. 30, 2020, which issued during the prosecution of Applicant's PCT/IL2019/051401.
An English Translation of an Office Action dated Jun. 2, 2020, which issued during the prosecution of Chinese Patent Application No. 201780051968.9.
Communication dated Oct. 21, 2019 from the United State Patent and Trademark Office in U.S. Appl. No. 15/540,664.
Communication dated Feb. 3, 2020 by the European Patent Office in application No. 17814898.7.
An ISR and Written Opinion issued in PCT/IL2019/051401, dated Jun. 24, 2020.
An EP Communication in Appl. No. 17814898.7, dated Oct. 5, 2020.

* cited by examiner

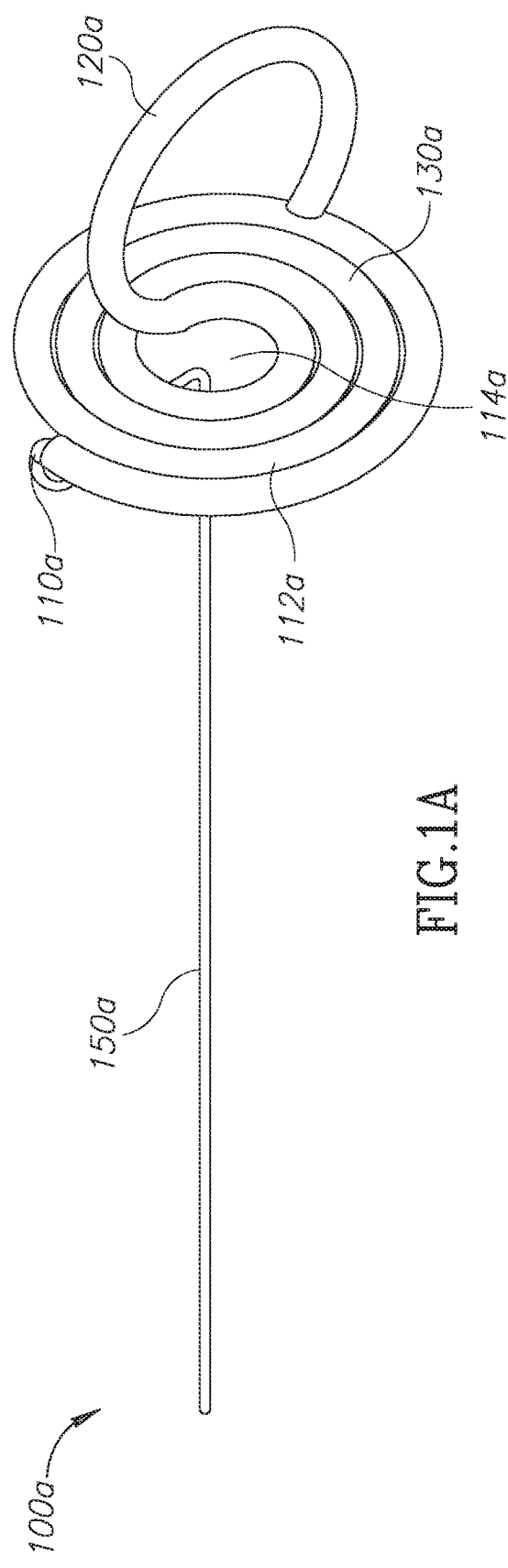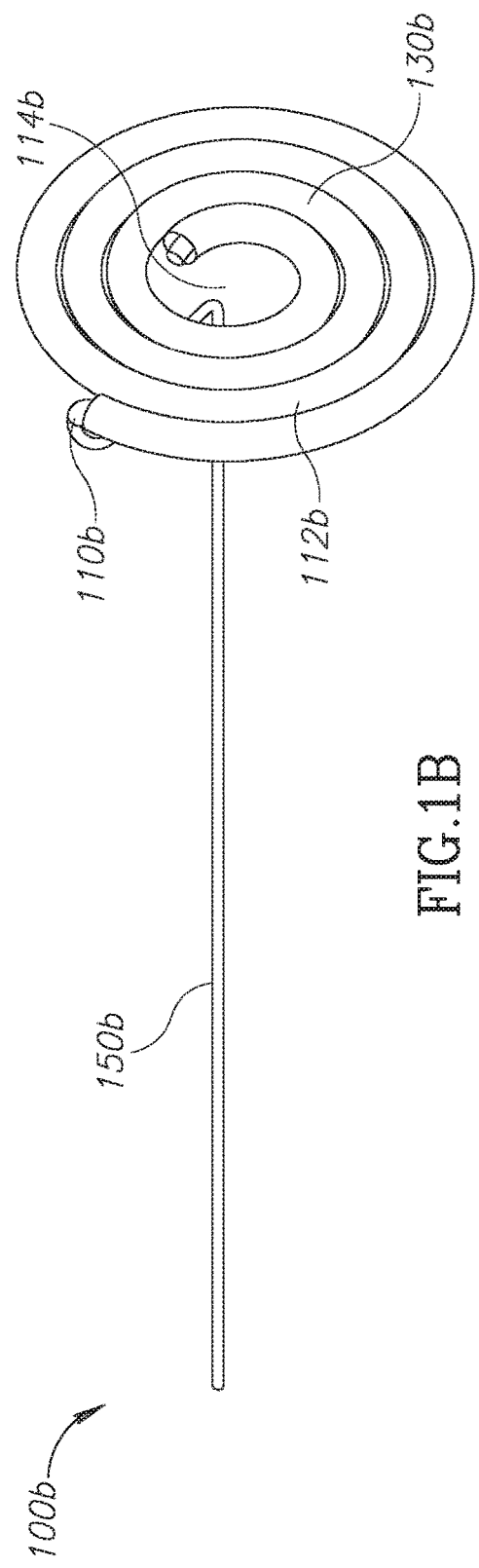
FIG.1A
FIG.1B

MEDICAL DEVICE FOR TREATING VASCULAR MALFORMATIONS

CROSS-REFERENCE TO RELATED APPLICATIONS

The present application is the U.S. national stage of International Application PCT/IL2017/050694, filed Jun. 21, 2017, which claims priority from U.S. Provisional Application 62/444,963, filed Jan. 11, 2017 and U.S. Provisional Application 62/352,578, filed Jun. 21, 2016, all of which are assigned to the assignee of the present application.

TECHNICAL FIELD

The present disclosure generally relates to the field of vascular malformations, such as aneurysms and restriction of blood flow thereto.

BACKGROUND

An aneurysm is an abnormal local dilation of an artery caused by a weakening of the artery wall. In the past, cerebral aneurysms were frequently treated by direct surgical intervention. For example, by installing a clip around the base of the aneurysm to prevent passage of blood between the aneurysm and the lumen of the vessel. Attempts have then been made to develop minimally invasive techniques for treating such aneurysms, for example, by filling the aneurysm with coils, such that the aneurysm eventually becomes a solid mass of coils and thrombus.

SUMMARY

The present disclosure relates to a device and methods for treating the human vasculature, such as but not limited to vascular malformations, aneurysms, vessel occlusions.

Advantageously, the device disclosed herein, includes a coiled section, which, due to its pre-shaped form, is configured to restrict/occlude blood flow into the aneurysm, thereby isolating the aneurysm from the normal circulation without blocking off any arteries nearby or narrowing the main vessel.

According to some embodiments, there is provided a device for treating a vascular malformation, the device comprising a wire having a coilable section configured to be coiled into a coil positionable within the vascular malformation; wherein the coil comprises a spiral or sequence of concentric loops; and wherein the coil is configured to line and/or bridge a neck of the vascular malformation so as to at least partially cover an orifice thereof, when in use.

According to some embodiments, the device further includes an anchoring section. According to some embodiments, the anchoring section may be external, i.e. configured to be located in the parent vessel, thereby anchoring the coilable section within the vascular malformation. According to some embodiments, the anchoring/docking section may be configured to form a secondary structure circumferentially lining a wall of the blood vessel, when in use.

According to some embodiments, there is provided a non-occlusive device for treating a vascular malformation, the device comprising a wire comprising: a coilable section configured to be coiled into a coil positionable within the vascular malformation; wherein said coil comprises a sequence of concentric loops; and wherein said coil is configured to line/bridge a neck of the vascular malformation so as to at least partially cover an orifice thereof, when in use; and a docking section configured to be positioned within the vascular malformation; wherein the docking section is configured to anchor and/or stabilize and/or assist the positioning of the device within the vascular malformation and/or to intertwine detachable coils delivered to the aneurysm, when in use. According to additional or alternative embodiments, the docking section, which is the first section of the wire that is configured to exit the delivery microcatheter and potentially contact the aneurysm wall, may function as an atraumatic tip to the device. The docking section may therefore be structured without exposed sharp and/or pointed edges (which may injure the aneurysm wall).

According to some embodiments, the coilable section may be essentially perpendicular to the anchoring/docking section, when deployed. According to some embodiments, the coiled section may be essentially parallel to the anchoring/docking section, when deployed.

According to some embodiments, the coil may include an aperture essentially in a center thereof. According to some embodiments, the aperture may be configured to at least partially lay over the orifice of the vascular malformation.

According to some embodiments, the coilable section may further include an outer cover covering at least part of the first section. According to some embodiments, the second section may be devoid of the cover. According to some embodiments, the cover may be radio-opaque and/or thrombogenic.

According to some embodiments, the anchoring section may be internal, i.e. positioned within the vascular malformation and configured to serve as a docking section for docking detachable coils delivered thereto, in which case the anchoring section is also referred to as a docking section. According to some embodiments, the docking section may be configured to assist in the folding of the coiled section and/or in its positioning within the vascular malformation (i e lining/bridging an aneurysm neck). According to some embodiments, the docking section is configured to anchor the device within the vascular malformation by entangling or otherwise associating with detachable coils delivered to the malformation, with the and/or through docking section. According to some embodiments, the docking section may be configured to intertwine detachable coils delivered to the aneurysm, when in use. According to some embodiments, due to the coiled section lining the neck of the aneurysm and/or due to the positioning of the docking section within the aneurysm sac, the device need not extend into the parent vessel, thereby significantly reducing the risk of blocking small blood vessels (i.e. perforator arteries such as lenticulostriate arteries adjacent cerebral aneurysms), a risk common to flow diverting devices. By not covering the blood vessel wall, the need for anti-platelet therapy, frequently required when using embolization devices (e.g. stents) so as to minimize aggregation of platelets and ultimately formation of thrombus in the parent vessel may be obviated. This is of particular importance when treating ruptured aneurysms in which case anticoagulant treatment is prohibited.

According to some embodiments, the device may be used in conjunction with any embolic agent. Additionally or alternatively, the device may be used in conjunction with detachable coils (e.g. Guglielmi detachable coils (GDCs)), in which case it may assist in holding the detachable coils in place and prevent their protrusion/herniation into the parent vessel. This is of particular importance when treating wide-neck aneurysms, which otherwise require stents or other structures positioned within the parent vessel to hold the detachable coils in place.

In some embodiments, the device may include an intermediate section (interconnecting the coiled section and the anchoring section). The intermediate section may be a swivel configured to enable the coiled section to revolve without turning the anchoring section, and thus to form the neck-lining spiral after the anchoring of the anchoring section within the aneurysm sac.

According to some embodiments, the diameter of the wire at a distal end of the first section may be larger than the diameter of the wire at a proximal end of the first section, such that the wire is tapered at the first section thereof.

According to some embodiments, the coilable section and the anchoring/docking section are formed from a single wire. Advantageously, by being formed of a single looped wire, the positioning of the device within the malformation is simplified as it implicates implanting only a single device. The production costs of such device is likewise significantly reduced.

According to some embodiments, the anchoring/docking section may be formed from the distal most part of the wire. According to some embodiments, the anchoring/docking section may be configured to form one or more loops when exiting catheter with which it is delivered. According to some embodiments, the anchoring/docking section may be ring shaped, when deployed. According to some embodiments, the anchoring/docking section may be hook shaped, when deployed.

According to some embodiments, the loops of the anchoring/docking section may be essentially perpendicular to the loops of the coiled section, when in their deployed form.

According to some embodiments, the coilable section of the wire and/or the anchoring/docking section of the wire may include two strands. According to some embodiments, in the coilable section the two strands may be braided. According to some embodiments, in the coilable section the two strands may be non-braided.

According to some embodiments, the wire may be bent and/or folded into a two-strand wire.

According to some embodiments, the coilable section of the wire may include two strands. According to some embodiments, the two strands may be substantially joined together along essentially the entire length of the coilable section, such that the coil is formed from the two-stranded wire.

According to some embodiments, the anchoring/docking section of the wire may include two strands forming a secondary structure. According to some embodiments, the secondary structure may be a double stranded helix.

According to some embodiments, the vascular malformation is a wide-neck aneurysm.

According to some embodiments, the coilable section, when deployed, enables controlling the deployment and/or positioning of the device within the aneurysm from a central axis thereof.

According to some embodiments, the coil has a form of a bowl when deployed and/or when not restrained. According to some embodiments, the coil has a form of a flat plate, when deployed and/or when not restrained.

According to some embodiments, the coilable section and/or the docking section may be made of a memory shape alloy.

According to some embodiments, the coilable section and/or the docking section may be made of a super elastic alloy.

According to some embodiments, the coilable section and/or the docking section may be made of a platinum-based alloy such as platinum iridium, platinum tungsten etc. and may or may not have a core wire.

According to some embodiments, the distal end of the coilable section forms an innermost loop of the coil and a proximal end of the coilable section forms an outermost loop of the coil.

According to some embodiments, the proximal end of the coilable section forms an innermost loop of the coil and a distal end of the coilable section forms an outermost loop of the coil.

According to some embodiments, the force exerted by the coilable section on a catheter configured to deliver the device to the blood vessel is gradually changing along a length ofi the coilable section.

According to some embodiments, the force exerted on the catheter by a distal end of the coilable section is weaker than the force exerted on the catheter by a proximal part of the coilable section.

According to some embodiments, the force exerted on the catheter by a distal end of the coilable section is stronger than the force exerted on the catheter by a proximal part of the coilable section.

According to some embodiments, the diameter of the wire at a distal end of the coilable section is smaller than the diameter of the wire at a proximal end of the coilable section, such that the wire has a tapered shape at the coilable section thereof.

According to some embodiments, the diameter of the wire at a distal end of the coilable section is larger than the diameter of the wire at a proximal end of the coilable section, such that the wire has a tapered shape at the coilable section thereof.

According to some embodiments, the coil comprises an aperture essentially in a center thereof. According to some embodiments, the aperture is sized and shaped to allow passage of a microcatheter delivering embolic material therethrough, such as but not limited to detachable coils.

According to some embodiments, the coilable section and/or anchoring/docking further comprises a core wire. According to some embodiments, the anchoring/docking section is devoid of the core wire. According to some embodiments, the core-wire is radio-opaque and/or thrombogenic. According to some embodiments, the core wire has a form of a coil coiled around at least the coilable section of the wire.

According to some embodiments, the coil has a gradually decreasing diameter. According to some embodiments, the coil has a gradually increasing diameter.

According to some embodiments, there is provided a kit for treating a vascular malformation, the kit comprising a device for treating the vascular malformation, the device comprising a wire comprising: a coilable section configured to be coiled into a coil positionable within the vascular malformation; wherein the coil comprises a spiral or sequence of concentric loops; and wherein the coil is configured to line a neck of the vascular malformation, so as to at least partially cover an orifice thereof, when in use; and a anchoring/docking section; and an embolic material configured for delivery through an aperture of the coil. According to some embodiments, the anchoring/docking section may be configured for position within the vascular malformation According to some embodiments, the anchoring/docking section may be configured to assist in the deployment of the coiled section and/or in its positioning of the coil within the vascular malformation (i.e. lining/bridging an aneurysm neck). According to some embodiments, the anchoring/ docking section may be configured to anchor the device within the vascular malformation, when in use.

According to some embodiments, the kit further comprises a microcatheter configured to deliver the device to a target area.

According to some embodiments, there is provided a method for treating a wide-neck aneurysm, the method comprising: deploying and/or positioning a neck-lining, coil assisting device within the wide-neck aneurysm, such that the device lines/bridges the neck of the aneurysm; and delivering an embolic material to the wide-neck aneurysm through an aperture in the neck-lining device, thereby preventing escape of embolic material through the neck of the wide-neck aneurysm; wherein the neck-lining device comprises a coilable section configured to be coiled into a coil when deployed; wherein the coil comprises a spiral or sequence of concentric loops.

According to some embodiments, the device further includes an anchoring/docking section, as essentially described herein.

According to some embodiments, the neck-lining device further comprises an anchoring/docking section, According to some embodiments, the anchoring/docking section is configured to anchor and/or stabilize and/or assist in the positioning of the device within the wide-neck aneurysm. Each possibility is a separate embodiment.

According to some embodiments, there is provided a device for treating vascular malformations in blood vessels, the device comprising a wire configured to coil into a coil positionable within the vascular malformation, the coil configured to line/bridge a neck of the vascular malformation, so as to at least partially cover an orifice thereof, wherein the device is devoid of elements extending into or positioned within a parent vessel adjacent the vascular malformation.

According to some embodiments, the coil has a gradually increasing diameter. According to some embodiments, the coil has a gradually decreasing diameter.

According to some embodiments, the device is configured to be positioned within the vascular malformation in its entirety.

According to some embodiments, there is provided a kit for treating a vascular malformation, the kit comprising: a device for treating the vascular malformation, the device comprising a wire configured to coil into a coil when deployed, the coil configured to line/bridge a neck of the vascular malformation, so as to at least partially cover an orifice thereof, wherein the device is devoid of elements extending into or positioned within a parent vessel adjacent the vascular malformation; and an embolic material configured for delivery through an aperture of the coil or alongside thereof.

According to some embodiments, the wire may be replaced with a strip.

According to some embodiments, the coilable section may be twisted into a twisted strip prior to it being coiled into a coil.

According to some embodiments, the strip may be split to form two strands. According to some embodiments, the split may be formed such that the sum of the widths of the two strands is about the same as the width of the strip. According to some embodiments, the two strands may be formed by cutting out an inner part of the strip, such that a sum of the widths of the two strands is less than the width of the strip.

According to some embodiments, the strip may be tapered, such that the width of a first end of the strip forming the coilable section is larger than the width of a second end of strip forming the anchoring/docking section.

According to some embodiments, the strip, for example at the end thereof forming the coiled section may include one or more cut-outs configured to reduce the rigidity thereof.

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some or none of the enumerated advantages.

BRIEF DESCRIPTION OF THE DRAWINGS

Examples illustrative of embodiments are described below with reference to figures attached hereto. In the figures, identical structures, elements or parts that appear in more than one figure are generally labeled with a same numeral in all the figures in which they appear. Alternatively, elements or parts that appear in more than one figure may be labeled with different numerals in the different figures in which they appear. Dimensions of components and features shown in the figures are generally chosen for convenience and clarity of presentation and are not necessarily shown in scale. The figures are listed below.

FIG. 1A depicts a device for treating vascular malformations including an internal anchor, according to some embodiments;

FIG. 1B depicts a device for treating vascular malformations devoid of an internal anchor, according to some embodiments;

DETAILED DESCRIPTION

Figure 2:
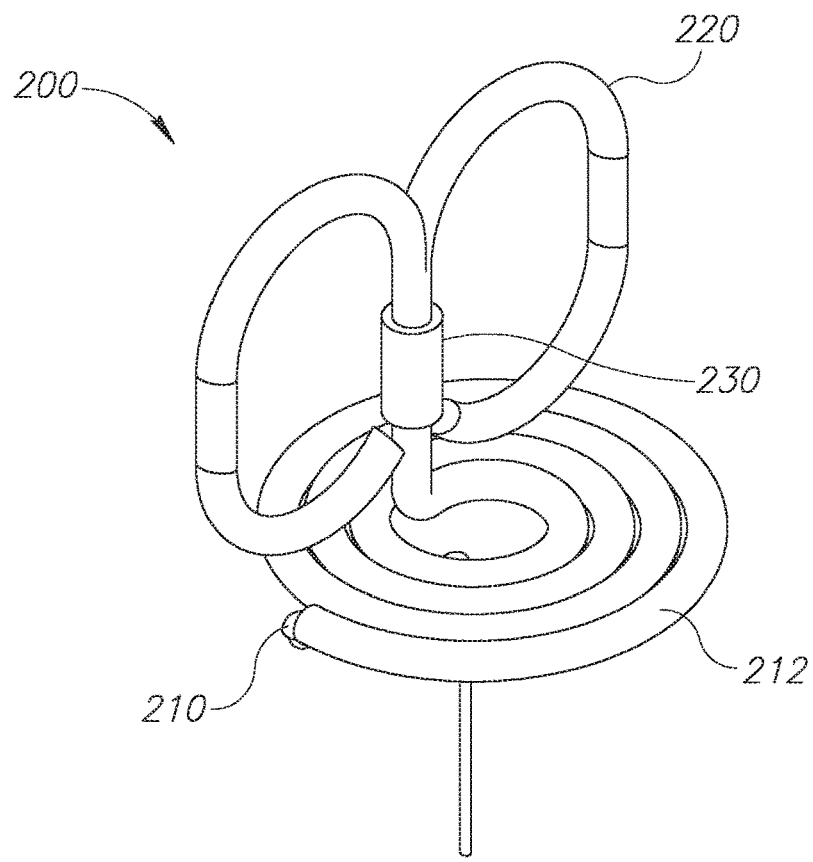
FIG. 2 depicts a device, including an internal anchor, for treating vascular malformations, according to some embodiments.

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

There is provided, according to some embodiments, a device for treating vascular malformations in blood vessels, the device including a wire having a coiled section and an anchoring section.

As used herein, the term "anchoring section" may refer to a part of the device configured to anchor the coilable part of the device within a vascular malformation for example such that the coiled part of the device lines the neck of the vascular malformation. Additionally or alternatively, the term may refer to the part of the device configured for docking detachable coils delivered to the vascular malformation, in which case the anchoring section may also be referred to as a "docking section". According to some embodiments, the anchoring section may be internal, i.e. configured for positioning within the vascular malformation so as to serve as an internal anchor and/or docking site. Alternatively, the anchoring section may be external, i.e. configured for positioning outside the vascular malformation, within the vascular malformation.

The coiled section is configured to coil into a coil positionable within the vascular malformation. According to some embodiments, the coil may be a spiral or sequence of rings. According to some embodiments, the spiral or sequence of rings may have a gradually increasing diameter. According to some embodiments, the spiral or sequence of rings may have a gradually decreasing diameter. The coil may be configured to line/bridge a neck of the vascular malformation and/or to line the wall thereof, so as to at least partially cover an orifice thereof.

According to some embodiments, the anchoring section is configured to form a second coil when deployed. According to some embodiments, the anchoring section may be formed from the most distal part of the wire. Alternatively, anchoring section may be molded to joined or otherwise attached to the distal end of the wire forming the coiled section. As used herein, the term "distal end" may refer to the end of the wire, which is the first to exit the micro catheter with which it is delivered and/or the end of the wire, which is first introduced to the aneurysm sac, when in use.

According to some embodiments, the anchoring/docking section may be configured to form one or more concentric loops when exiting the catheter with which it is delivered.

According to some embodiments, the loops of the anchoring/docking section may be essentially perpendicular to the loops of the coiled section, when in its deployed form.

According to some embodiments, the anchoring/docking section may be made from a same or a different material. As a non-limiting example, the docking section may include, be formed of, or covered by an at least partially radiopaque material, such as, but not limited to, tantalum, gold, tungsten, platinum or any combination thereof, and/or may have radiopaque markers. Each possibility is a separate embodiment.

According to some embodiments, the anchoring/docking section may be configured to serve as an entangle element, anchoring the device within the vascular malformation and/or docking detachable coils delivered thereto by being intertwined and/or interlaced with the detachable coils.

According to some embodiments, the device may be formed of a single wire or a design that allows it to behave like a single wire. Such configuration enables the delivery of the device through a catheter having an internal diameter of below 0.69 millimeters. This is in contrast to occlusion devices such as cage type structures formed of collapsed elements, which are expanded upon deployment and/or positioning. It is noted that although the diameters provided hereinabove are typically suitable for neurovasculature, other sizes/diameters that may be used for any other endovascular application are also within the scope of this disclosure.

As used herein the term "vascular deformation" and "vascular malformation" may be used interchangeably and may refer to any congenital and/or non-congenital blood vessel abnormality, such as, but not limited to, aneurysms, fistulas, tumors and arteriovenous malformations. Each possibility is a separate embodiment. Aneurysms are a result of a weakened blood vessel wall, and can be a result of a hereditary condition or an acquired disease. If left untreated, an aneurysm can rupture, leading to life threatening situations. For example, a ruptured aneurysm may cause intracranial hemorrhage, which can result in death or severe neurologic deficit. In some patients, aneurysms can put pressure on nerves or brain tissue, causing pain, abnormal sensations, and/or seizures.

According to some embodiments, the aneurysm may be a saccular aneurysm formed in the wall of blood vessels, most typically arteries. The aneurysm may be described as a blood-filled balloon-like sac having a neck, which leads into the parental vessel. While aneurysms can occur in any blood vessel of the body, a large percentage of aneurysms are found in cerebral arteries. Thus, according to some embodiments, the aneurysm may be a cerebral aneurysm, such as, but not limited to, berry aneurysms, wide-neck aneurysms, giant aneurysms, dissecting aneurysms and fusiform aneurysms. Each possibility is a separate embodiment. According to some embodiments, the vascular malformation may be a wide-neck aneurysm. According to some embodiments, the vascular malformation may be a ruptured aneurysm. Additional non-limiting examples of aneurysms include coronary artery aneurysms, ventricular aneurysms, aneurysm of sinus of Valsalva, and aneurysms following cardiac surgery, aortic aneurysms including thoracic aortic aneurysms and abdominal aortic aneurysms, intraparechymal aneurysms and capillary aneurysms. Each possibility is a separate embodiment. According to some embodiments, the aneurysm may be an aneurysm formed at or near a bifurcation, where a main vessel branches into two or more separate vessels. Aneurysms, at or near bifurcations, present unique challenges to successful treatment.

As used herein the term "neck" with referral to vascular malformation refers to the base of the aneurysm closest to the parent vessel. The neck may be distinct or indistinct.

As used herein the terms "orifice", "opening" and "ostium" may be used interchangeably and refer to the opening between the aneurysm and the parent vessel.

According to some embodiments, the device, disclosed herein, may be non-occlusive. According to some embodiments, the device may be a blood restricting device. As used herein the term "non-occlusive device" may refer to a device which alters the flow of blood into the aneurysm but which does not necessarily impede blood flow into the malformation. According to some embodiments, the non-occlusive device may be a flow-altering device. According to some embodiments, the device is configured to restrict flow into the aneurysm. According to some embodiments, the device is configured to facilitate a restricted flow of blood into the vascular malformation. According to some embodiments, the term "restricted flow" may refer to a flow of blood altered in its direction, pressure or speed. According to some embodiment, a restricted flow of blood may refer to a flow of blood being reduced by 10%-50%, 50%-60%, 50%-70%, 80%, 90% or more as compared to the flow of blood into the untreated aneurysm. Each possibility is a separate embodiment. According to some embodiments, at least 10%, 20%, 30%, 40% or more of the pre-treatment blood flow into the aneurysm is maintained after treatment. Each possibility is a separate embodiment.

According, to some embodiments, the device may be configured to be delivered through a microcatheter. According to some embodiments, when deployed from the catheter, the device assumes its pre-determined configuration.

According to some embodiments, the device may be a stand-alone device. That is, the device alone may be sufficient for treatment of aneurysms.

According to some embodiments, the device may be a coil assisting device which may be used in conjunction with standard coils, also referred to herein as "filler coils", "embolization coils" and "detachable coils", such as, but not limited to, Guglielmi detachable coils (GDC). According to some embodiments, the term "detachable coils" may refer to coils configured to fill and/or be packed into the vascular malformation. The detachable coils promote blood clotting around the coils, thereby eventually sealing the aneurysm and reducing pressure on its wall.

According to some embodiments, the device may be suitable for minimally invasive treatments of aneurysms. Additionally or alternatively, the device may be used to cause vessel occlusion for treatment of aneurysms, for restricting hemorrhages for reducing blood supply to tumors and/or any other condition for which vessel occlusion is desired. Each possibility is a separate embodiment. According to some embodiments, the device may be configured to support and/or be anchored within the aneurysm sac.

As used herein the term "coil formed" may refer to a sequence or spiral of rings having a gradually decreasing or increasing diameter. According to some embodiments, the coiled section and/or the anchoring/docking section may be non-braided. Advantageously, by being non-braided, the risk of perforating caused by unraveling of a braided cage formed implants is avoided. Consequently, no securing caps configured to hold together the ends of the braid are needed, allowing the coilable sections to form essentially smooth configurations without protrusions. In addition, coilable wires have a lower delivery profile as compared to braided or other implants. This since the wire requires minimal catheter lumen diameter, thereby allowing easier access to the neurovasculature. Yet another advantage is the ability to re-sheath the wire in case the operator is not satisfied with its deployment, and/or if re-deployment or exchange for a different device size is needed. Also, the time and place of detachment of the device may be accurately controlled by operating a pusher. According to some embodiments, the wire may have a diameter of below 0.65, 0.6, 0.5, 0.3, 0.15 or 0.1 mm along the length thereof. Each possibility is a separate embodiment. It is noted that although the diameters provided hereinabove are typically suitable for neurovasculature, other sizes/diameters that may be used for any other endo vascular application are also covered under the scope of this disclosure.

According to some embodiments, the coiled section may be sized and shaped to line the aneurysm sac. According to some embodiments, the coiled section may line approximately one third of the aneurysm sac, closest to the parent vessel. According to some embodiments, the coiled section may be essentially bowl-shaped. According to some embodiments, the coiled section may be sized and shaped to line the neck of an aneurysm. According to some embodiments, the coil may be sized and shaped to line the neck of a wide-neck aneurysm, thereby holding detachable coils, delivered to the aneurysm, in place.

According to some embodiments, the coiled section may include an aperture (opening) essentially in the center thereof. According to some embodiments, the aperture may at least partially line the orifice of the vascular malformation, when in use. According to some embodiments, the aperture may be sized and shaped to allow passage of detachable coils therethrough.

According to some embodiments, the coiled section may be devoid of prongs, clips or any other protrusions, which may be thrombogenic. According to some embodiments, the shape and/or positioning of the coiled section may be obtained/stabilized by the docking section for example due to a force exerted by the anchoring section thereon.

According to some embodiments, the coiled section, configured to form the coil, may have a proximal end and a distal end. According to some embodiments, the distal end of the coiled section may be configured to form the outermost ring of the coil.

According to some embodiments, the proximal end of the coiled section may be configured to form the innermost ring of the coil. According to other embodiments, the distal end of the coiled section may be configured to form the innermost ring of the coil. According to some embodiments, the proximal end of the coiled section may be configured to form the outermost ring of the coil.

According to some embodiments, the diameter of the wire's coilable section may be gradually changing along a length thereof. According to some embodiments, the force exerted on a catheter (used for delivering the wire) by the wire's coilable section may be gradually decreasing from its proximal to its distal end. According to other embodiments, the force exerted on a catheter by the wire's coilable section may be gradually increasing from its proximal to its distal end. According to other embodiments, the force applied on a catheter by a distal end of the wire's coilable section may be weaker than the force applied on a catheter by a proximal part of the wire's coilable section. According to other embodiments, the force applied on a catheter by a distal end of the wire's coilable section may be stronger than the force applied on a catheter by a proximal part of the wire's coilable section. According to some embodiments, the diameter of the wire forming the coilable section's distal end is smaller than the diameter of the wire forming the coilable section's proximal part. According to other embodiments, the diameter of the wire forming the coilable section's distal end is larger than the diameter of the wire forming the coilable section's proximal part.

According to some embodiments, the wire may be a tube (hollow). According to some embodiments, the coilable section of the tube may have variable pitch along the length thereof. This may be achieved, for example, by a plurality of cuts, such as, but not limited to, laser cuts. According to some embodiments, the plurality of cuts may be configured to reduce the force applied by the coilable section's distal end of the tube on a catheter. According to some embodiments, the force exerted on a catheter (delivering the wire) by the wire's coilable section may be decreasing from its proximal to its distal end by using a sleeve covering the proximal part/end of the wire. According to other embodiments, the force exerted on a catheter (delivering the wire) by the wire's coilable section may be increasing from its proximal to its distal end by using a sleeve covering the proximal part/end of the wire. According to some embodiments, the device is formed from a wire, which is a spring/coil defining a primary wind, wherein looped first and second sections form secondary winds. The proximal section of the coil includes a core wire threaded there through. As a result, the distal part of the coil applies a lower force on the catheter than the force applied by the proximal part of the coil.

According to some embodiments, the diameter of the wire's coilable section may be configured to avoid "pig-tailing" of the catheter when introducing the device to the blood vessel.

According to some embodiments, the wire may be formed of a single plate and/or strip, the strip having a coilable section configured to be coiled into a coil positionable within the vascular malformation; and a docking section which when deployed form one or more loops essentially perpendicular to the loops of the coil. By being formed of a single twisted and/or coiled plate/strip, rather than intertwined wires, problems due to corrosiveness as well as pig-tailing may be reduced.

According to some embodiments, the term "approximately" may refer to +/−0.5%, +/−1%, +/−2%, +/−5%, or +/−10%. Each possibility is a separate embodiment.

According to some embodiments, the anchoring/docking section may be sized and shaped to facilitate anchoring of the device within the vascular malformation. According to some embodiments, the anchoring/docking section may assume a looped shape when deployed/positioned within the malformation. According to some embodiments, the anchoring section may form a tertiary structure contributing to the deployment, anchoring, stabilization and/or positioning of the device within the malformation. According to some embodiments, the anchoring/docking section or a distal end thereof may be coiled into a shape resembling that of detachable coils, thereby in itself serving as an embolic material. According to some embodiments, the anchoring/docking section may be configured to entangle or be entangled by detachable coils delivered to the malformation, thereby anchoring and/or bolstering the anchoring of the device within the aneurysm.

According to some embodiments, the wire forming the device may be made of a memory shape material (e.g. a memory shape alloy or a memory shape polymer). According to some embodiments, the wire forming the device may include a memory shape alloy material. According to some embodiments, the wire forming the device may include a metal covered by a memory shape alloy material governing the shape of the metal. According to some embodiments, the wire forming the device may be made of a temperature sensitive memory shape material configured to assume its desired configuration upon exposure to body temperature.

According to some embodiments, the wire forming the device may be made of a super elastic material. According to some embodiments, the wire forming the device may include a super elastic material. According to some embodiments, the wire forming the device may include a metal covered by a super elastic material governing the shape of the metal. According to some embodiments, the super elastic may include platinum, nickel titanium (nitinol), tungsten or any combination thereof. Each possibility is a separate embodiment.

According to some embodiments, the device may include, be formed of, or covered by an at least partially radiopaque material, such as, but not limited to, tantalum, gold, tungsten or platinum, or have radiopaque markers. Each possibility is a separate embodiment. According to some embodiments, the radiopaque material may enable visualization in CT scans, X-rays and the like. According to some embodiments, the wire including the outer radio-opaque coating may have a diameter of below 0.65, 0.5, 0.45, 0.4, 0.35, 0.3 or 0.25 mm along the length thereof. Each possibility is a separate embodiment.

According to some embodiments, in its un-deployed form, within the catheter, the device may have a form of a straight wire. As used herein, the term "straight wire" may refer to an un-winded wire, a wire with a primary wind and/or a wire with a secondary wind. According to some embodiments, the term "straight wire" may refer to the device prior to having reached its tertiary configuration. It is thus understood, that during deployment and/or positioning, the wire loops to form its desired configuration. According to some embodiments, the wire may loop into its desired configuration without requiring radial expansion.

According to some embodiments, the size of the coiled section and/or the anchoring/docking section may be adjustable. According to some embodiments, the size and shape of the coiled section may be varied dependent on the type and/or size of the aneurysm to be treated. For example, to treat a relatively small berry aneurysm in cranial arteries, the coiled section may be relatively small; to treat significantly larger aneurysms in larger vessels, a larger coiled section may be used. According to some embodiments, the shape of the coiled section may be round, oval, elliptic or any other suitable shape fitting the shape of the aneurysm sac or parts thereof. Each possibility is a separate embodiment.

According to some embodiments, the wire may further include an intermediate section formed between the coiled section and the anchoring section. According to some embodiments, the intermediate section is or includes a swivel configured to enable the coiled section to revolve without turning the anchoring section. That is, the anchoring section, serving as an internal anchor may be positioned within the vascular aneurysm whereafter positioning of the coilable section and its coiling is enabled, without causing twist of the anchoring section.

According to some embodiments, the coiled section, the anchoring/docking section and/or the intermediate section may be made of a same material, such as, but not limited to, platinum, tungsten or combinations thereof. Each possibility is a separate embodiment. According to some embodiments, the coiled section, the anchoring section and/or the intermediate section may be made from different materials.

According to some embodiments, the device may further include a drug eluting material. According to some embodiments, the device or parts thereof, such as the coiled section, the anchoring section and/or the intermediate section, may be coated with a drug eluting material. Each possibility is a separate embodiment. According to some embodiments, the device may include a drug eluting compartment configured to release a drug within the aneurysm, at the aneurysm neck. Non-limiting examples of suitable drugs include Paclitaxel, Sirolimus and/or Everolimus. Each possibility is a separate embodiment.

According to some embodiments, the coiled section may include filaments (e.g. synthetic filaments) or other elements configured to add thrombogenicity and/or facilitate coil entanglement. A non-limiting example of suitable filaments includes urethane strands. According to some embodiments, the filaments may be an integral part of the coiled section. According to some embodiments, the filaments may be attached to the coiled section using any suitable attachment method known in the art.

According to some embodiments, there is provided a device for treating vascular malformations in blood vessels, the device including a wire configured to coil into a coil positionable within the vascular malformation, the coil configured to line/bridge a neck of the vascular malformation and/or to line the wall thereof, so as to at least partially cover an orifice thereof. According to some embodiments, the coil may have a gradually increasing diameter. According to some embodiments, the coil may have a gradually decreasing diameter.

According to some embodiments, the device is configured to be positioned within the vascular malformation in its entirety. According to some embodiments, the device may be devoid of elements extending into or positioned within the parent vessel adjacent the vascular malformation. According to some embodiments, the device is configured to coil into a single coil. According to some embodiments, the device consists of a wire configured to coil into a coil positionable within the vascular malformation, the coil configured to line a neck of the vascular malformation and/or to line the wall thereof, so as to at least partially cover an orifice thereof.

According to some embodiments, the coil has a form of a bowl when deployed and/or when not restrained. According to some embodiments, the coil has a form of a flat plate, when deployed and/or when not restrained.

According to some embodiments, the wire is made of a memory shape alloy. According to some embodiments, the wire is made of a super elastic alloy.

According to some embodiments, a distal end of the part of the wire forming the coiled section forms the innermost loop of the coil and the proximal end of the part of the wire forming the coiled section forms an outermost loop of the coil, as essentially described herein.

According to some embodiments, the diameter of the wire or of part of the wire forming the coiled section is gradually increasing from a proximal to a distal end thereof. According to some embodiments, the diameter of the wire or of part of the wire forming the coiled section is gradually decreasing from a proximal to a distal end thereof.

According to some embodiments, the coil has an aperture essentially in a center thereof. According to some embodiments, the aperture is sized and shaped to allow passage of detachable coils therethrough, as essentially described herein.

According to some embodiments, the wire includes a core wire and an outer cover, covering at least part thereof. According to some embodiments, the cover is radio-opaque and/or thrombogenic. According to some embodiments, the cover has a form of a coil, coiled around at least the coiled section of said wire.

Figure 3:
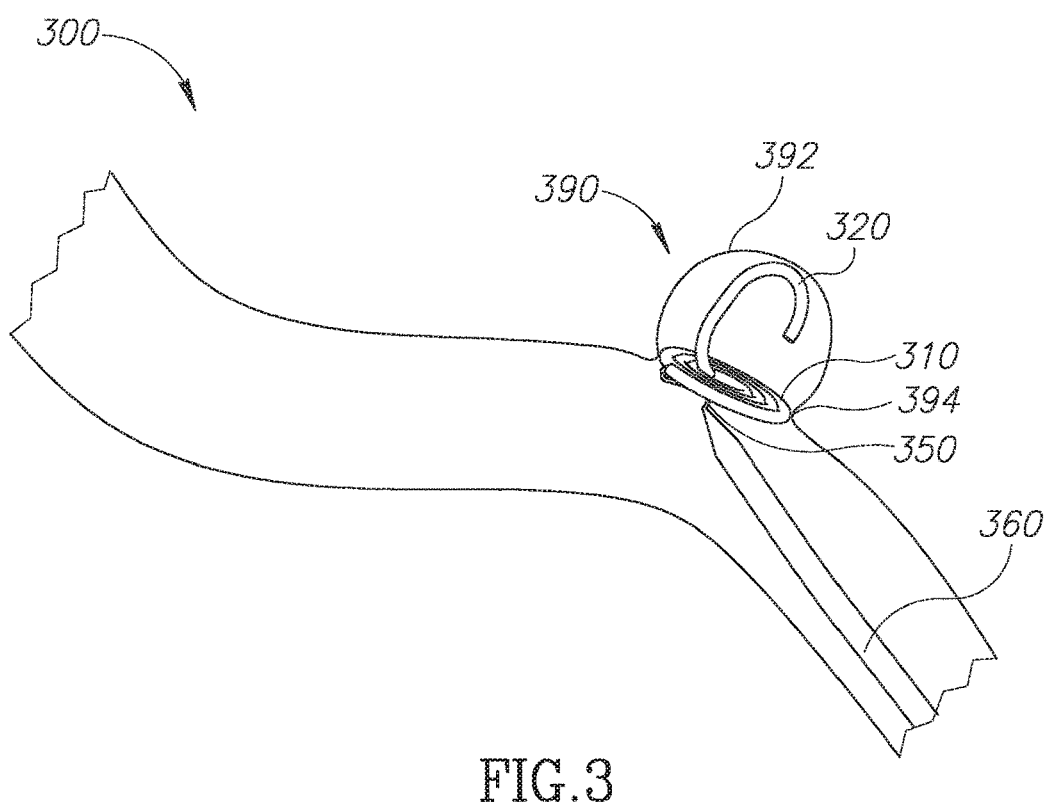
FIG. 3 depicts the device of FIG. 1 positioned within a wide-neck aneurysm, according to some embodiments.
Figure 4:
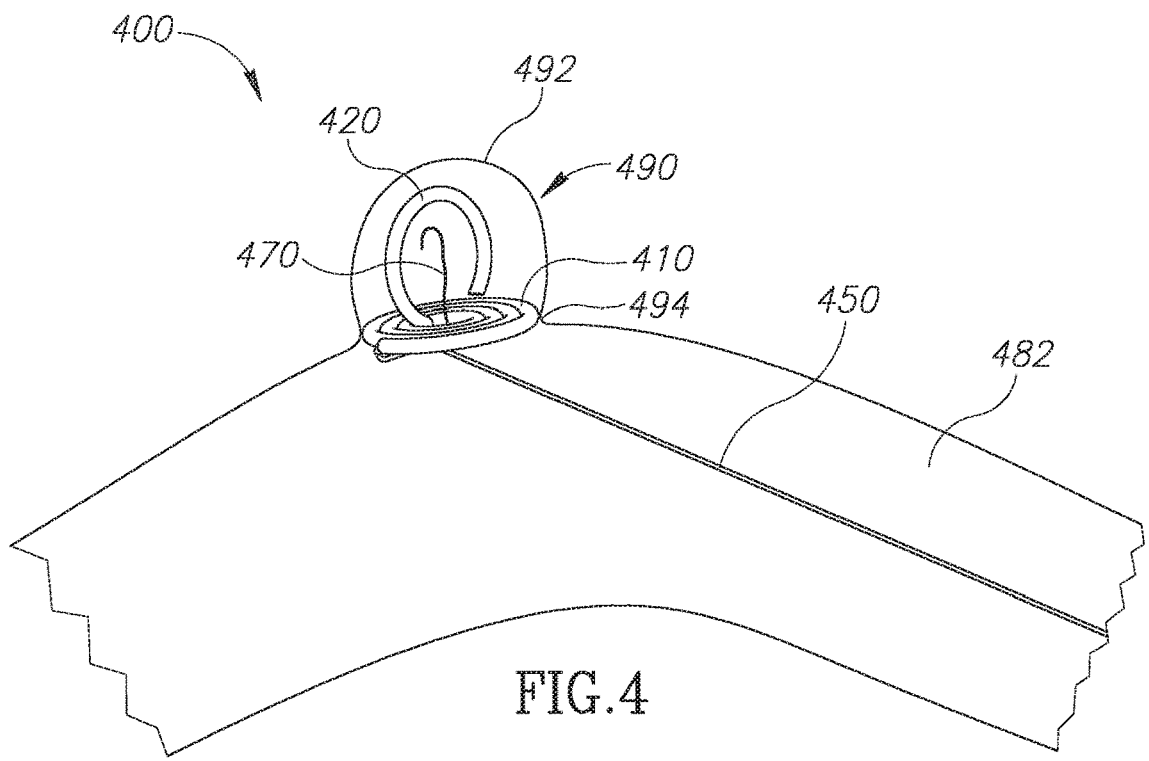
FIG. 4 depicts the device of FIG. 1, positioned within a wide-neck aneurysm during delivery of a detachable coil, according to some embodiments.
Figure 5:
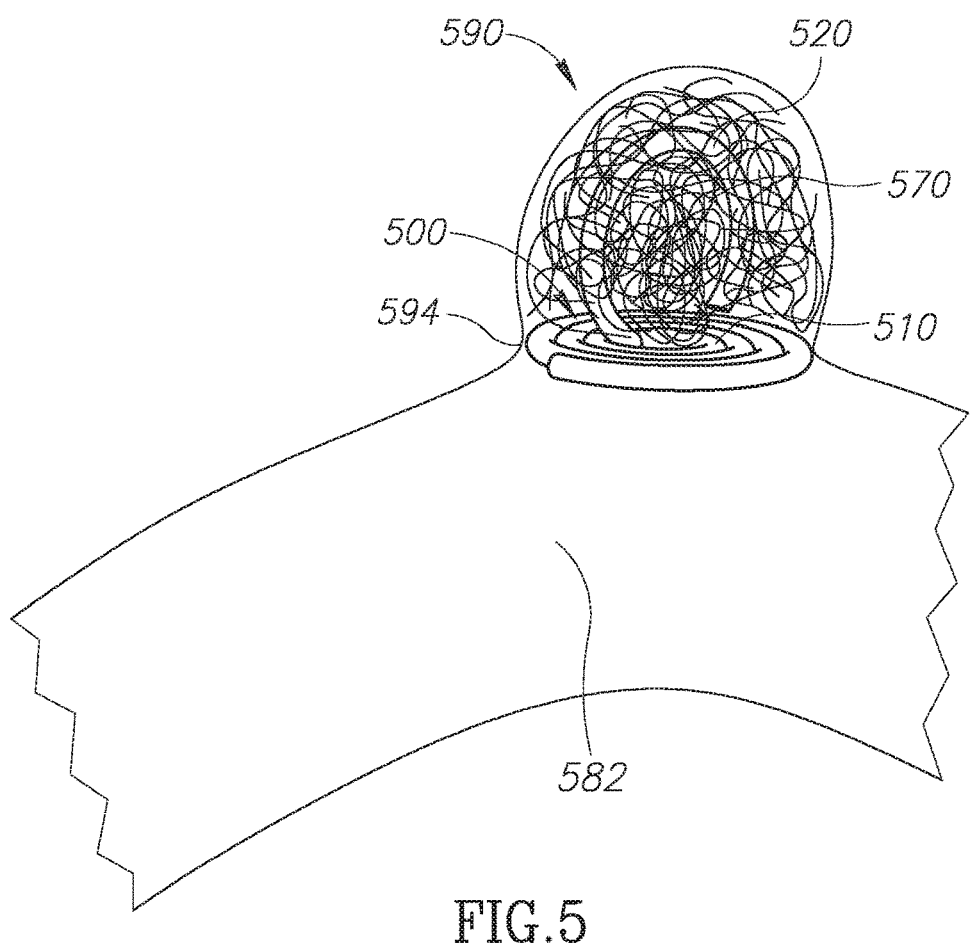
FIG. 5 depicts the device of FIG. 1, positioned within a wide-neck aneurysm filled with detachable coils; according to some embodiments.

Reference is now made to FIG. 1A, which schematically illustrates a device 100a for treating vascular malformations, in its expanded/desired form, according to some embodiments. In its non-expanded form, device 100a is essentially a straight wire (configuration not shown), configured to fit within a microcatheter. Device 100a has three sections, namely a coiled section 110a forming a coil, a hook shaped anchoring section 120a and an intermediate section 130a interconnecting coiled section 110a and anchoring section 120a. The coil of coiled section 110a is configured to line the neck of an aneurysm, and anchoring section 120a to anchor device 100a within the aneurysm, as illustrated in FIG. 3-5. Coiled section 110a includes an aperture 114a essentially in the center thereof. Aperture 114a is configured to at least partially line the orifice of the aneurysm and to allow passage of detachable coils therethrough, as illustrated in FIG. 4. In this way, detachable coils may be safely delivered to aneurysms, including wide-neck aneurysms, without the risk of protrusion/herniation. Optionally, coiled section 110a may be covered by a cover, such as opaque cover 112a. Opaque cover 112a is here illustrated as a sheet, however other configurations, such as a cover in the form of a coil or a braid or the like is also applicable and within the scope of this disclosure. Similarly, anchoring section 120a is here shown to be hook shaped, but other configurations are also applicable and within the scope of this disclosure. Similarly, the anchoring section may include more than on hook or loops/hooks and such configurations are likewise within the scope of the disclosure. According to some embodiments, anchoring section 120a may at least partially line the dome and/or wall of the aneurysm, as shown in FIG. 3. Alternatively, anchoring section 120a may be positioned within the aneurysm without contacting the walls and/or dome thereof, as illustrated in FIG. 4. According to some embodiments, anchoring section 120a may serve as an entanglement element configured to entangle detachable coils delivered through the aneurysm, as shown in FIG. 5.

Reference is now made to FIG. 1B, which depicts a vessel occluding device 100b, in its expanded/desired form, according to some embodiments. In its non-expanded form, device 100b is essentially a straight wire (configuration not shown), configured to fit within a microcatheter. Device 100b has a coiled section forming coil 110b. The coil of coiled section 110b is configured to line the neck of an aneurysm, and includes an aperture 114b essentially in the center thereof. Aperture 114b is configured to at least partially line the orifice of the aneurysm and to allow passage of detachable coils therethrough. In this way, detachable coils may be safely delivered to aneurysms, including wide-neck aneurysms, without the risk of coils exiting the aneurysm and being released into the parent vessel. Optionally, coiled section 110b may be covered by a cover, such as opaque cover 112b. Opaque cover 112b is here illustrated as a sheet, however other configurations, such as a cover in the form of a coil or a braid or the like is also applicable and within the scope of this disclosure.

Devices 100a and 100b may be positioned in an aneurysm by tethers/pushers 150a and 150b, respectively, which enable steering devices 100a and 100b from the center axes thereof, such that coiled sections 110a and 110b line the neck of the aneurysm and anchoring section 120a of FIG. 1a is placed within the aneurysm sac.

Reference is now made to FIG. 2, which schematically illustrates a device 200 for treating vascular malformations, in its expanded/desired form, according to some embodiments. In its non-expanded form, device 200 is essentially in a shape of a straight wire (configuration not shown), configured to fit within a microcatheter. Device 200 is formed of three sections, namely a coiled section 210, a looped anchoring section 220, and an intermediate section 230 interconnecting coiled section 210 and anchoring section 220. The coil of coiled section 210 is configured to line the neck of an aneurysm, and double looped anchoring section 220 to anchor device 200 within the aneurysm. Intermediate section 230, includes as a swivel and is configured to enable coiled section 210 to revolve into its coiled form without turning of anchoring section 220. Anchoring section 220 is here shown to form two loops, but other configurations are also applicable and within the scope of this disclosure. According to some embodiments, anchoring section 220 may line the wall of the aneurysm essentially circumferentially. Optionally, coiled section 210 may be covered by a cover, such as radiopaque cover 212. Radiopaque cover 212 is here illustrated as a sheet, however other configurations, such as a cover in the form of a coil or a braid or the like is also applicable and within the scope of this disclosure.

Reference is now made to FIG. 3, which schematically illustrates a device 300 for treating vascular malformations, positioned within a wide-neck aneurysm 390, according to some embodiments. Device 300 is delivered through catheter 360 and guided by tether/pusher 350 into aneurysm 390, where it assumes its expanded/desired configuration. That is, coiled section 310 is coiled into a coil, which lines the neck 394 of aneurysm 390, while anchoring section 320 (also referred to herein as an internal anchor) assumes its hook shaped configuration which contacts the dome 392 of aneurysm 390, and anchors device 300 within aneurysm 390. The positioning of device 300 is controlled through tether/usher 350, which is connected to device 300 at the center thereof, as best seen in FIG. 1-3, thereby enabling relatively easy steering of device 300 into its desired positon within aneurysm 390.

Reference is now made to FIG. 4, which schematically illustrates a device 400 for treating vascular malformations, positioned within a wide-neck aneurysm 490, according to some embodiments. Device 400 is positioned by help of tether/pusher 450, which enables steering device 400 through the center axis thereof, such that coiled section 410 lines the neck 494 of aneurysm 490 and anchoring section (also referred to as an internal anchor) anchoring device 400 within aneurysm 490, here without contacting the dome 492 of aneurysm sac 490. Once securely positioned, an aperture (similar to aperture 114 of FIG. 1), formed essentially in the center of the coiled section 410, allows delivery of detachable coils, such as detachable coil 470 therethrough, while preventing protrusion/herniation of detachable coils into parent vessel 482. Coiled section 410 is coiled into a coil, which lines the neck 494 of aneurysm 490, while anchoring section 420 assumes its hook shaped configuration which does not contact the dome 492 of aneurysm 490 but is configured to lock/stabilize/tangle detachable coils, such as detachable coil 470 within aneurysm 490.

Figure 7:
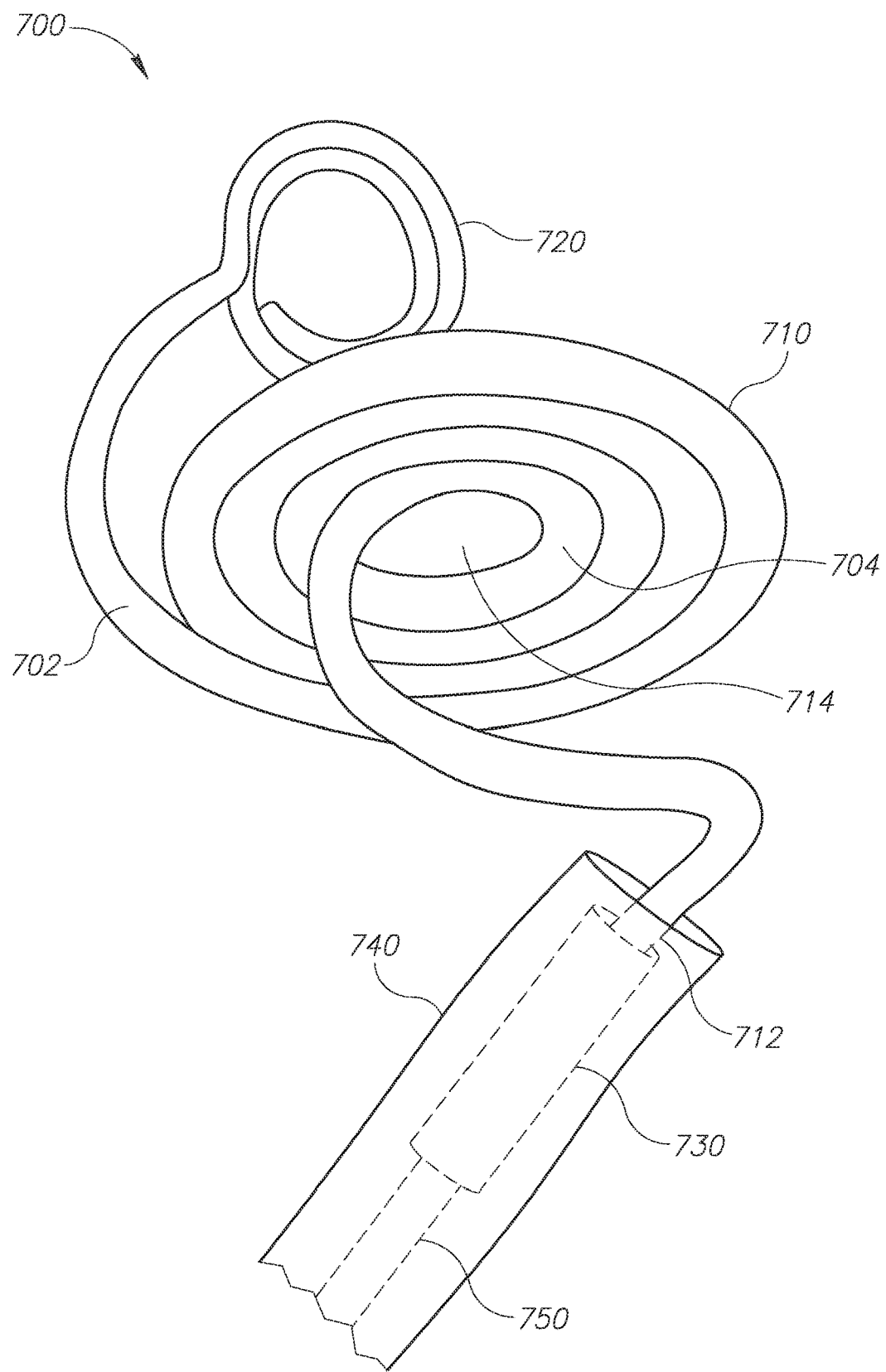
FIG. 7 depicts a device for treating vascular malformations including an internal docking section, according to some embodiments.

It is understood that other configurations of anchoring section, such as a looped shaped anchoring section, as illustrated in FIG. 7, is also applicable and within the scope of this disclosure. Similarly, device 400 is here illustratively shown to be essentially similar to device 300, however a similar positioning of other devices, such as device 700 illustrated in FIG. 7 is also applicable and as such within the scope of this disclosure.

Reference is now made to FIG. 5, which schematically illustrates a device 500 for treating vascular malformations, positioning within a wide-neck aneurysm 590 packed with detachable coils 570, according to some embodiments. Detachable coils 570, are delivered through an aperture in the coiled section 510 of device 500, as illustrated in FIG. 4 and are held in place by coiled section 570, which lines the neck 594 of aneurysm 590, thereby preventing their protrusion/herniation into the parent vessel. Coiled section 510 lines the neck 594 of aneurysm 590, while anchoring section 520 assumes its hook shaped configuration which is configured to lock/stabilize/tangle detachable coils 570 within aneurysm 590.

It is understood that other configurations anchoring section, such as a looped shaped anchoring section, as illustrated in FIG. 7, is also applicable and within the scope of this disclosure. Similarly, device 500 is here illustratively shown to be essentially similar to device 300, however a similar positioning of other devices, such as device 700 illustrated in FIG. 7 herein below is also applicable and as such within the scope of this disclosure.

Advantageously, device 500 is positioned within aneurysm 590 essentially without protruding into parent vessel 582. This may be of uttermost importance, in that blood clotting (thromboembolism) may form on stents or similar structures in the parent vessels. This risk is augmented when treating ruptured aneurysms in which case anticoagulant treatment may not be provided. Furthermore, by holding detachable coils 570 in place during delivery, the packing of aneurysm 590 may be improved, thereby reducing the risk of aneurysm regrowth due to residual neck.

Figure 6:
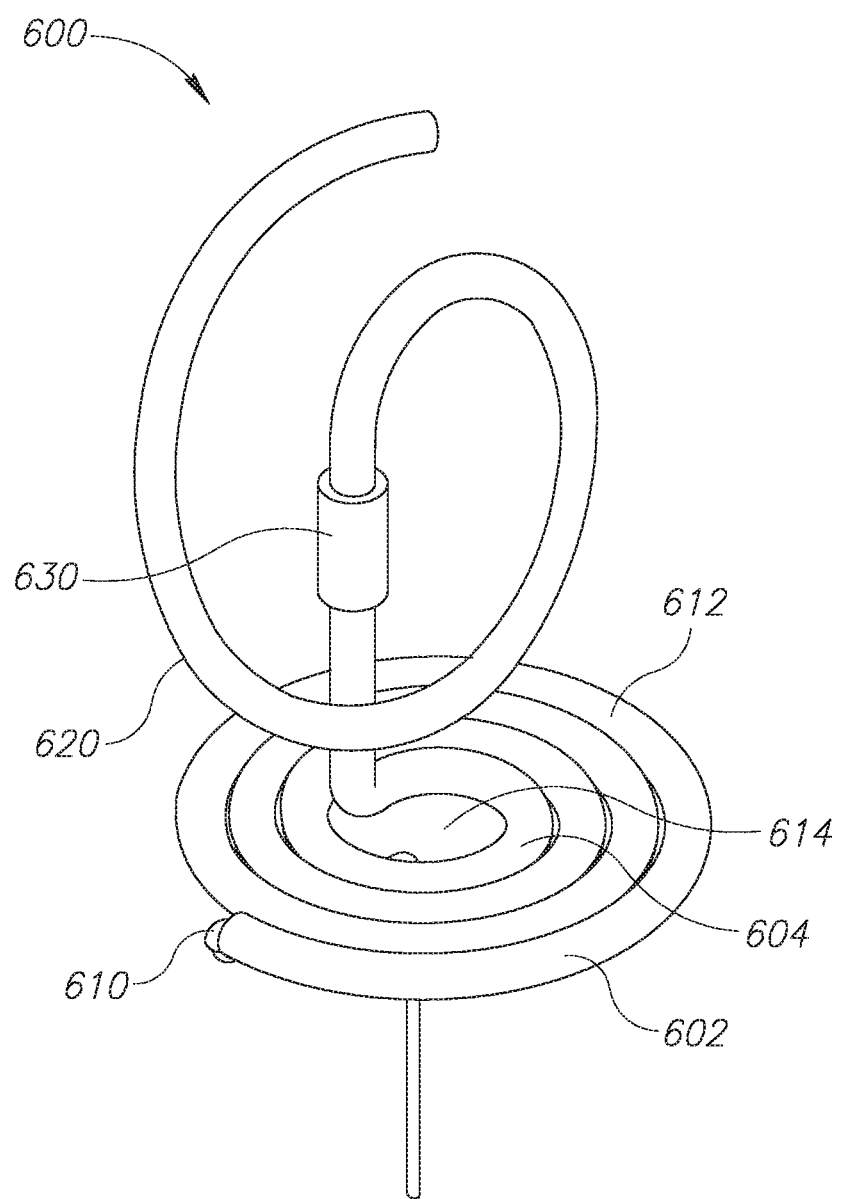
FIG. 6 depicts a device for treating vascular malformations including an internal anchor, according to some embodiments.

Reference is now made to FIG. 6, which schematically illustrates a device 600 for treating vascular malformations, in its expanded/desired form, according to some embodiments. In its non-expanded form, device 600 is essentially a straight wire (configuration not shown), configured to fit within a microcatheter. Device 600 has three sections, namely a coiled section 610 forming a coil, a spiral shaped anchoring section 620 and an intermediate section 630 interconnecting coiled section 610 and anchoring section 620. The coil of coiled section 610 is configured to line the neck of an aneurysm, and anchoring section 620 to anchor device 600 within the aneurysm. Intermediate section 630, includes as a swivel and is configured to enable coiled section 610 to revolve into its coiled form without turning of anchoring section 620. Coiled section 610 includes an aperture 614 essentially in the center thereof. Aperture 614 is configured to at least partially line the orifice of the aneurysm and to allow passage of detachable coils therethrough, as essentially illustrated in FIG. 4. In this way, detachable coils may be safely delivered to aneurysms, including wide-neck aneurysms, without the risk of protrusion/herniation. Optionally, coiled section 610 may be covered by a cover, such as radiopaque cover 612. Radiopaque cover 612 is here illustrated as a sheet, however other configurations, such as a cover in the form of a coil or a braid or the like is also applicable and within the scope of this disclosure. Similarly, anchoring section 620 is here shown to be spiral shaped, but other configurations are also applicable and within the scope of this disclosure. According to some embodiments, anchoring section 620 may at least partially line the dome and/or wall of the aneurysm, as shown in FIG. 3. Alternatively, anchoring section 620 may be positioned within the aneurysm without contacting the walls and/or dome thereof, as illustrated in FIG. 4. According to some embodiments, anchoring section 620 may serve as an entanglement element configured to entangle detachable coils delivered through the aneurysm, as shown in FIG. 5. When device 600 exits the microcatheter (not shown) and is placed in the aneurysm, the distal most section thereof, namely anchoring section 620, exits the microcatheter first. Next, coilable section 610 is formed into loops, such that the loops are formed around central aperture 614 of coilable section 610, forming a series of concentric loops. An innermost loop 604 is formed from the distal most section of coilable section 610. Coilable section 610 continues to form loops having gradually increasing diameters and finally with an outermost loop 602 having the largest diameter (among the loops of coilable section 610). When fully placed in the aneurysm, docking section 620 is located at a center of device 600. It is noted that although it is shown herein in FIG. 6 that the innermost loop is formed from the distal most section of coilable section 610, the scope of this disclosure also includes a device having a coilable section, wherein the distal most section thereof is the outermost loop (as for example, device 700 of FIG. 7).

Reference is now made to FIG. 7, which schematically illustrates a device 700 for treating vascular malformations, in its expanded/desired form, according to some embodiments. In its non-expanded form, device 700 is essentially a straight wire (configuration not shown), configured to fit within a microcatheter. Device 700 has two sections, namely a coilable section 710 forming a coil and a docking (anchoring) section 720, here in the form of one or two loops formed on the side of coiled section 710. When device 700 exits a microcatheter 740 and is placed in the aneurysm, the distal most section thereof, namely docking section 720, exits microcatheter 740 first. Next, coilable section 710 is formed into loops, such that the loops are formed around central aperture 714 of coilable section 710, forming a series of concentric loops. Coilable section 710 loops around a central aperture 714 thereof, forming a series of concentric loops. An outermost loop 702 is formed from the distal most section of coilable section 710. Coilable section 710 continues to form loops having gradually decreasing diameters and finally with an innermost loop 704 having the smallest diameter (among the loops of coilable section 710). When fully placed in the aneurysm, docking section 720 is located at a side of device 700. According to some embodiments, docking section 720 does not extend from the center of the concentric coils of coilable section 710. According to some embodiments, docking section 720 extends from outermost loop 702 of coilable section 710. It is noted that although it is shown herein in FIG. 7 that the outermost loop is formed from the distal most section of coilable section 710, the scope of this disclosure also includes a device having a coilable section, wherein the distal most section thereof forms the innermost loop (as for example, device 600 of FIG. 6). The coil of coiled section 710 is configured to at least partially line/bridge the neck of an aneurysm. Docking section 720 is configured to aid in the correct deployment and/or positioning of coiled section 710 within the aneurysm and optionally to anchor device 700 within the aneurysm. Aperture 714, which is located essentially in the center of coiled section 710, is configured to allow delivery of detachable coils therethrough, as essentially illustrated hereinbelow. In this way, detachable coils may be safely delivered to aneurysms, including wide-neck aneurysms, without the risk of protrusion/herniation. Optionally, coiled section 710 may include a core wire, such as a radiopaque core wire (not shown) Similarly, docking section 720 is here shown to form two loops, but other configurations are also applicable and within the scope of this disclosure. Similarly, docking section 720 is here shown to be essentially perpendicular to coiled section 710, however other configurations are also applicable and within the scope of this disclosure. Docking section 720 may be positioned within the aneurysm with or without contacting the walls and/or dome thereof. According to some embodiments, docking section 720 may serve as an entanglement element configured to entangle detachable coils delivered through the aneurysm, as illustrated herein below. Device 700 can be introduced to the aneurysm using micro catheter 740 for example in a manner similar to the embodiment illustrated in FIGS. 4 and 5. Once properly located in the aneurysm and/or when the medical process is completed, device 700 can be disconnected from a pusher wire 750 (which can be an integral part of device wire) by a disconnecting mechanism 730. It is noted that although not shown in FIG. 7, in accordance with some embodiments, a disconnected mechanism, such as disconnected mechanism 730 may be located at any location along coilable section 710, for example, proximally and in proximity (for example, in close proximity) to aperture 714, such that upon disconnection of pusher wire 750, device 700 terminates with innermost loop 704.

According to some embodiments, the anchoring/docking sections (such as but not limited to, anchoring/docking sections 120, 220, 420, 520, 620 and 720) are shown as having, for example, a ring/spiral/anchor/hook shape, but other configurations such as, S-shape, C-shape, random shape, etc. or any combination thereof, are also applicable and within the scope of this disclosure. Each possibility is a separate embodiment.

Figure 8A:
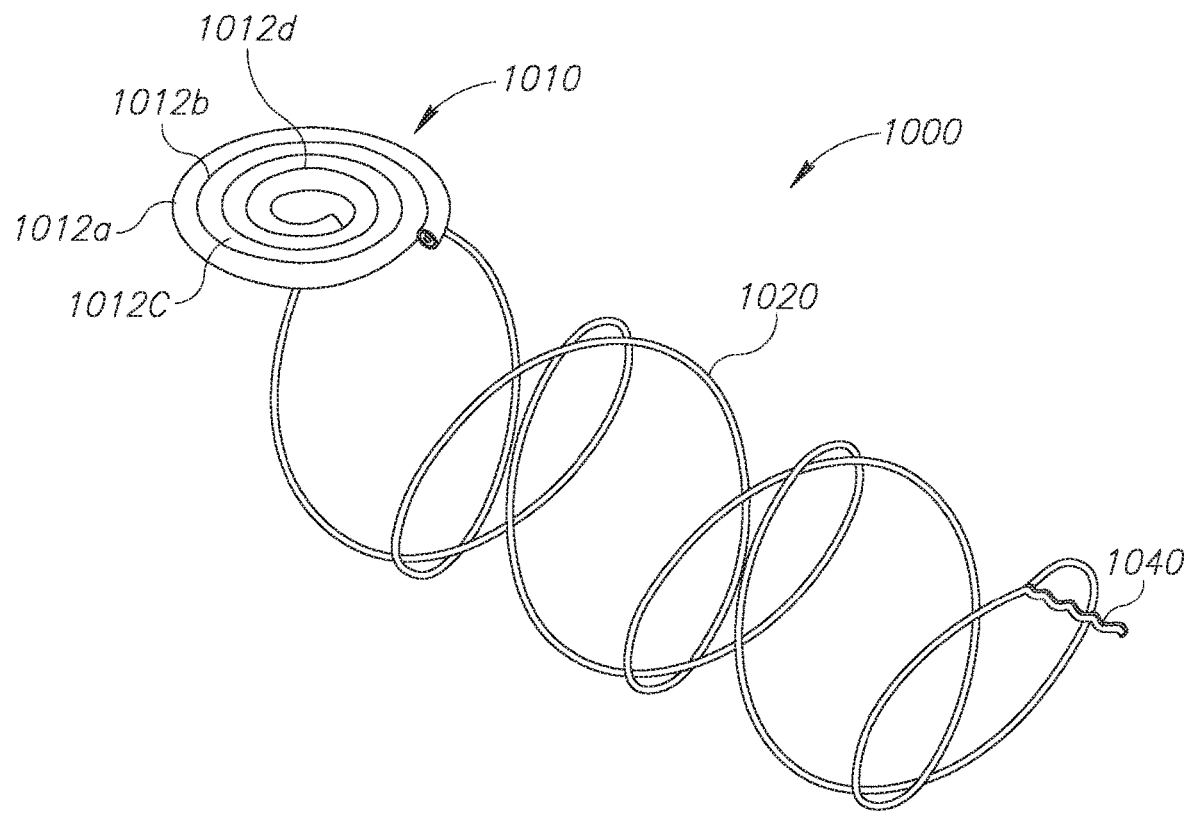
FIG. 8A schematically illustrates a perspective view of a device for treating vascular malformations including a double stranded wire, according to some embodiments.
Figure 8B:
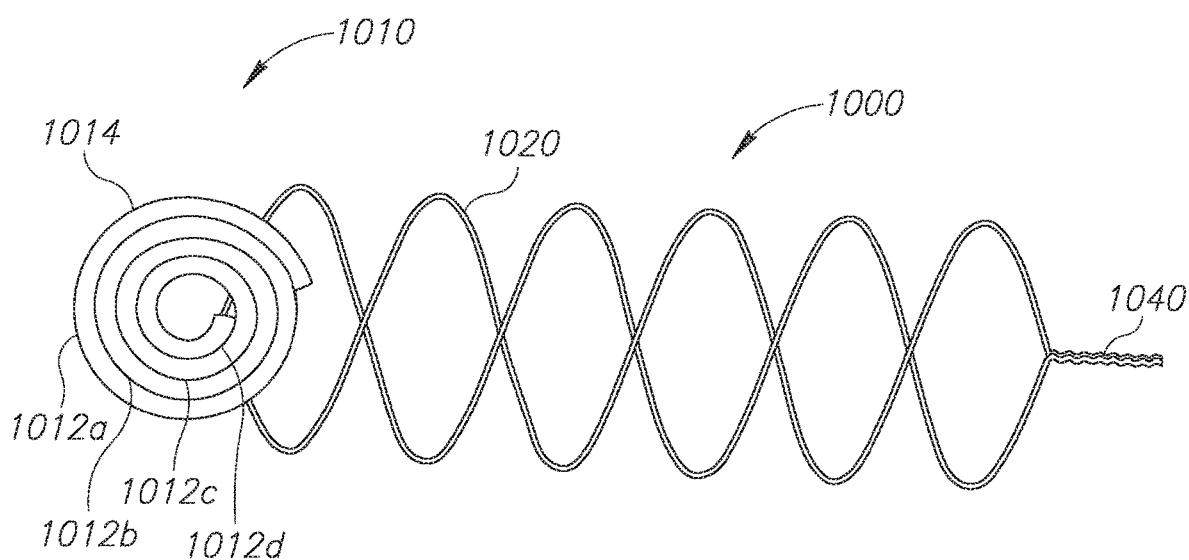
FIG. 8B schematically illustrates a top view of a device for treating vascular malformations including a two stranded wire, according to some embodiments.

Reference is now made to FIG. 8A and FIG. 8B, which schematically illustrate a device 1000 for treating vascular malformations, in its deployed/expanded form, according to some embodiments. Device 1000 has a first section 1010 configured to be positioned within a vascular malformation and a second section 1020 configured to circumferentially line and/or engage the parent vessel, adjacent the malformation. Device 1000 is formed from a single wire, bent or folded into a double stranded wire, the first end of which is illustrated as 1110 in FIG. 9A and FIG. 9B and the second end of which forming second section 1020. First section 1010 is here shown to be covered by a radiopaque material 1014 enabling visualization using imaging techniques such as CT, during implantation of device 1000. However, cover 1014 is optional and similar devices devoid of an outer coating are within the scope of the present disclosure. Device 1000 is here made from a single wire. However, according to some embodiments, device 1000 may be made from more than a single wire, e.g. 2, 3 or more wires and such configurations are likewise within the scope of the disclosure.

Along first section 1010 the two strands of double stranded wire 1110 are substantially joined (optionally braided) together along essentially the entire length of first section 1010 (not shown) and the joined (optionally braided) wires are together coiled into the form of a coil by looping the joined (optionally braided) wires into gradually decreasing loops, here illustratively depicted as four loops 1012a-

1012d. At an inner most loop, here loop 1012d, marking the beginning of second section 1020, the two strands of double stranded wire 1110 are separated from each other and coiled to form the double stranded helix.

Device 1000 further includes a delivery section 1040 configured to enable temporary attachment to a pusher wire assisting in the delivery of the device to a target location.

Figure 9A:
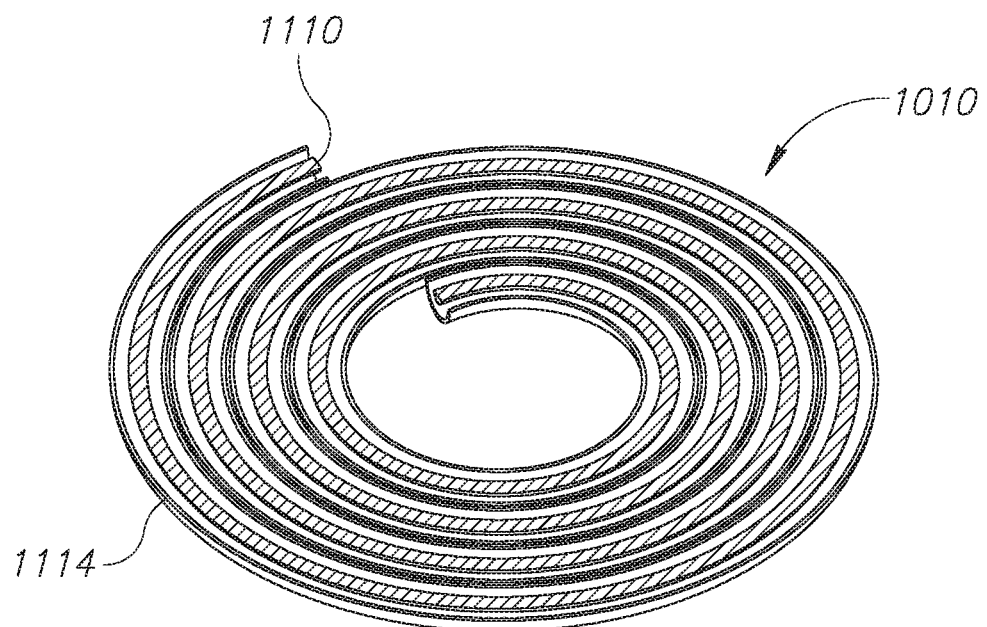
FIG. 9A schematically illustrates a horizontal cross section of the first section of the device of FIG. 1A and FIG. 1B.
Figure 9B:
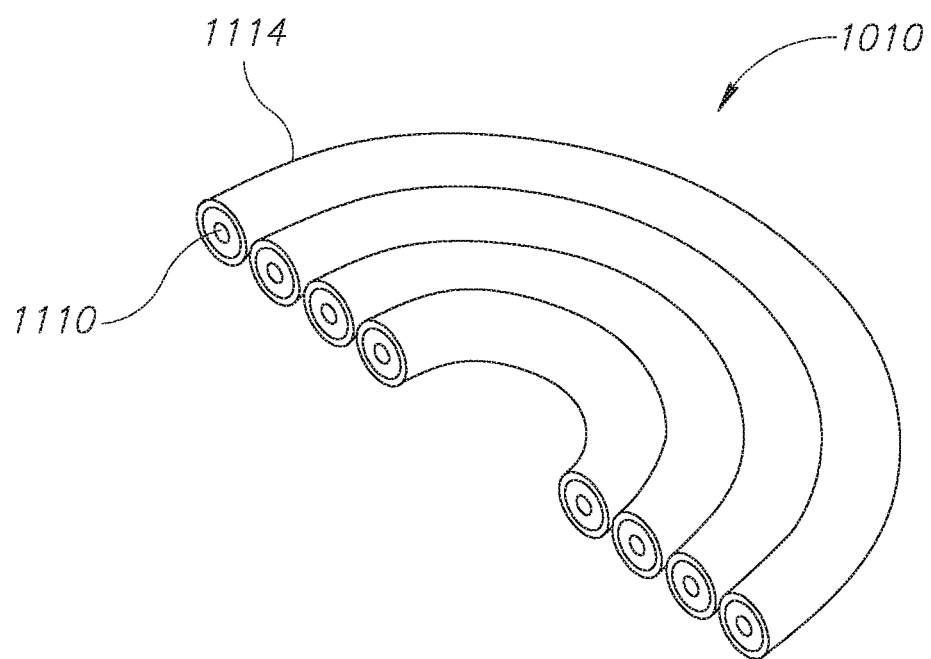
FIG. 9B schematically illustrates a vertical cross section of the first section of the device of FIG. 1A and FIG. 1B.

Reference is now made to FIG. 9A and FIG. 9B which schematically illustrate horizontal and vertical cross sections, respectively, of first section 1110 of device 1000, as depicted in FIG. 8A and FIG. 8B. Along first section 1010, the two strands of double stranded wire 1110 are joined together (optionally braided) along essentially the entire length of first section 1010. Double stranded wire 1110 is here further covered by an outer cover 1114 (corresponding to cover 1014 of FIG. 8A and FIG. 8B) preferably made from a radiopaque material enabling visualization during implantation as essentially described herein. Deployment and/or positioning of device 1000 causes double stranded wire 1010 and thus cover 1114 to coil into the form of a coil having gradually decreasing loops, as essentially described herein.

Figure 10A:
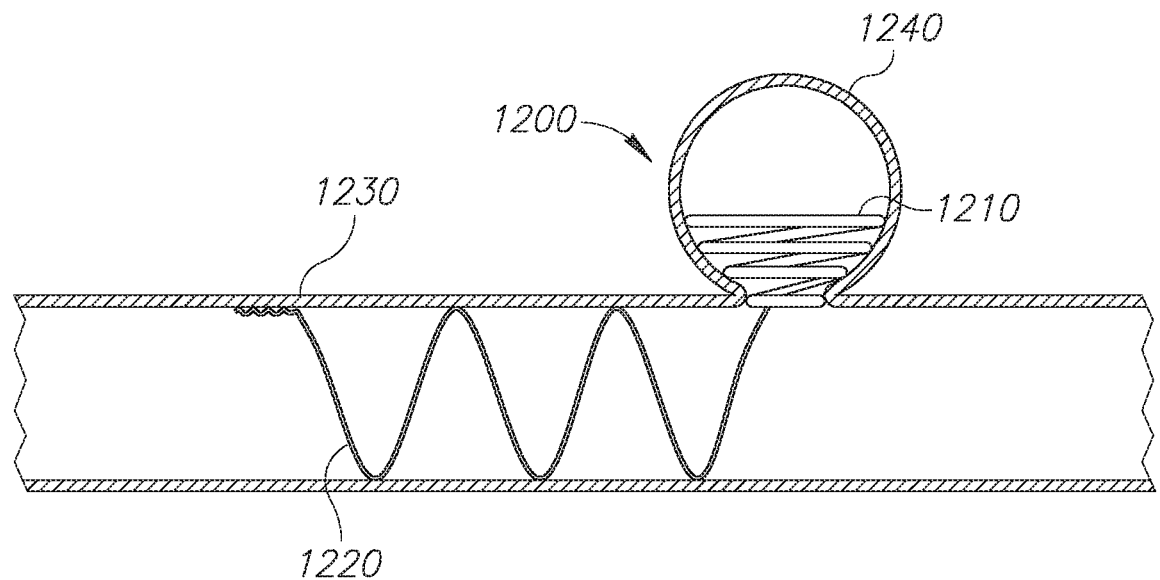
FIG. 10A schematically illustrates a perspective view of the device of FIG. 1A and FIG. 1B as positioned within a vascular malformation, according to some embodiments.
Figure 10B:
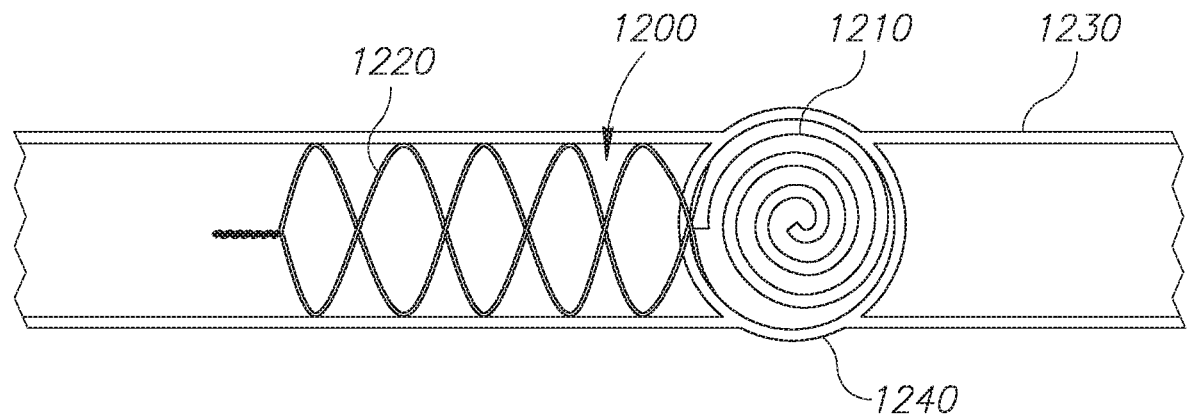
FIG. 10B schematically illustrates a top view of the device of FIG. 1A and FIG. 1B positioned within a vascular malformation, according to some embodiments.

Reference is now made to FIG. 10A and FIG. 10B, which show device 1200 deployed and positioned within a blood vessel 1230 with a vascular deformation 1240. First section 1210 of device 1200, coiled into a coil, is positioned within vascular malformation 1240, and second section 1220, forming a double stranded helix, circumferentially lines/engages an inner wall of blood vessel 1230, adjacent vascular malformation 1240, along a longitudinal axis thereof. It is understood that if device 1200 is formed from a single, double stranded wire, the deployment and/or positioning of device 1200 may be performed by a single move (e.g. by pulling the distal end of the wire), once first section 1210 reaches vascular malformation 1240. Furthermore, the double stranded helix of second section 1220 ensures firm attachment and/or positioning of device 1200 within blood vessel 1230.

Figure 11A:
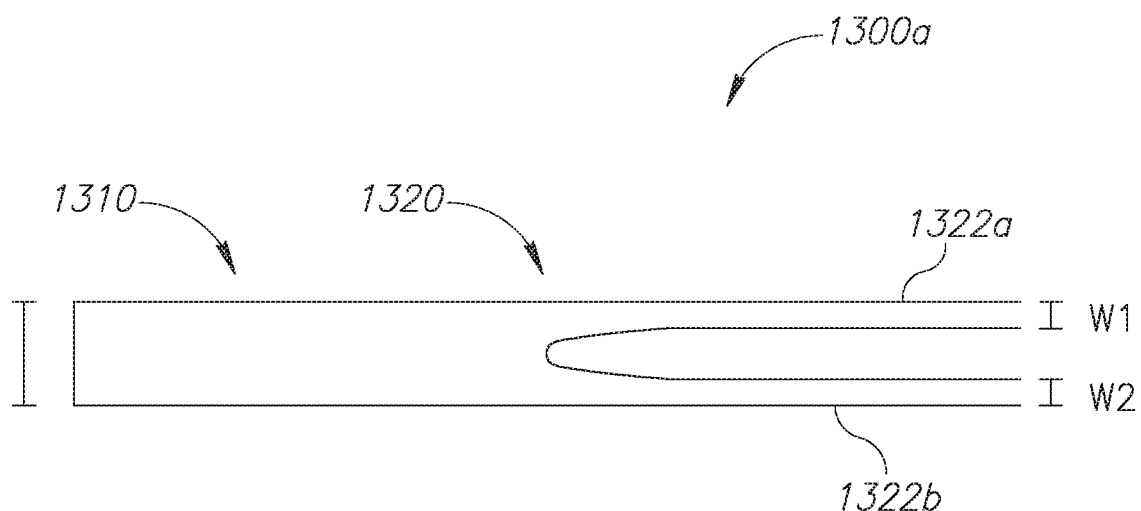
FIG. 11A schematically illustrates a single plate having a first section and a second section, the first section configured to be coiled into a coil positionable within a vascular malformation and the second section forming two strands which, when deployed, are configured to form a double stranded helix engaging the parent vessel.

Reference is now made to FIG. 11A which shows a single (straight) strip 1300a having a first section 1310 and a second section 1320. First section 1310 is configured to be twined into the form of a twisted strip and subsequently to be coiled into a coil suitable for positioning within a vascular malformation. Second section 1320 forms two strands 1322a and 1322b, which are configured to form a secondary structure (e.g. a double stranded helix) engaging an inner wall of a parent vessel, adjacent the malformation, when positioned. First section 1310 has a width W, which (upon twisting and coiling) is suitable for positioning within the vascular malformation without requiring additional coatings for its visualization during implantation (e.g. 0.4 mm). Strands 1322a and 1322b are formed by cutting out an inner part of strip 1300a, such that the sum of the widths w1 and w2 of strands 1322a and 1322b is less than width W of strip 1300a. As a non-limiting example, the width of strip 1300a may be 0.4 mm and an inner 0.2 mm may be cut out such that strands 1322a and 1322b each have a width of ~0.1 mm.

Figure 11B:
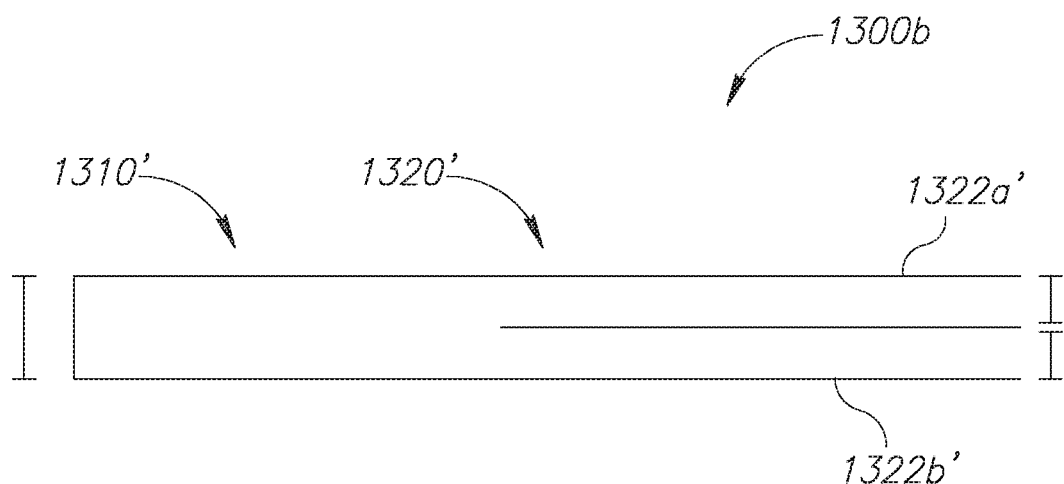
FIG. 11B schematically illustrates a single plate having a first section and a second section, the first section configured to be coiled into a coil positionable within a vascular malformation and the second section forming two strands which, when deployed, are configured to form a double stranded helix engaging the parent vessel.

Reference is now made to FIG. 11B which shows a single strip 1300b having a first section 1310' and a second section 1320'. First section 1310' is configured to be coiled into a coil suitable for positioning within a vascular malformation, and second section 1320', forming strands 1322a' and 1322b', is configured to form a secondary structure (e.g. a double stranded helix), suitable for engaging an inner wall of an adjacent blood vessel (the parent vessel—not shown). First section 1310' has a width W' (e.g. 0.2 mm), and is preferably covered by a radio opaque material (not shown) enabling its visualization during implantation. Strands 1322a' and 1322b' are formed by splitting strip 1300b, along second section 1320, at essentially the center thereof, such that the sum of the widths w1' and w2' of strands 1322a' and 1322b' will be essentially similar to width W' of strip 1300b. As a non-limiting example, the width of strip 1300b may be 0.2 mm at first section 1310', and strands 1322a' and 1322b' may each have a width of ~0.1 mm.

Figure 11C:
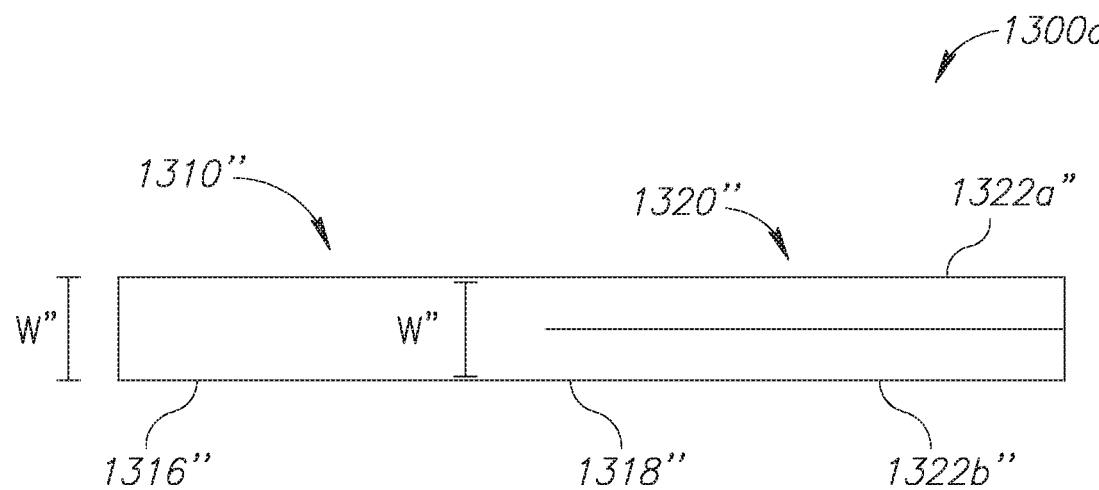
FIG. 11C schematically illustrates a single plate having a first section and a second section, the first section configured to be coiled into a coil positionable within a vascular malformation and the second section forming two strands which, when deployed, are configured to form a double stranded helix engaging the parent vessel.

Reference is now made to FIG. 11C which shows a single strip 1300c having a first section 1310" and a second section 1320". First section 1310" is configured to be coiled into a coil positionable within a vascular malformation, and second section 1320", forming strands 1322a" and 1322b", is configured to form a secondary structure (e.g. a double stranded helix), suitable for engaging an inner wall of an adjacent blood vessel (the parent vessel). First section 1310" is tapered along the length thereof, such that the width W" at the distal end 1316" of first section 1310" is wider than width w'" at a proximal end 1318" of first section 1310". This serves to ensure that the looping of first section 1310" is made easier as the loops to be formed are getting smaller. As a non-limiting example, the width of strip 1300c at distal end 1316" of first section 1310" may be 0.4 mm and then gradually tapered to 0.2 mm at distal end 1318" of first section 1310'. Strands 1322a" and 1322b" having a width of ~0.1 mm may then be obtained by splitting second section 1320", as essentially described in FIG. 13B.

Figure 11D:
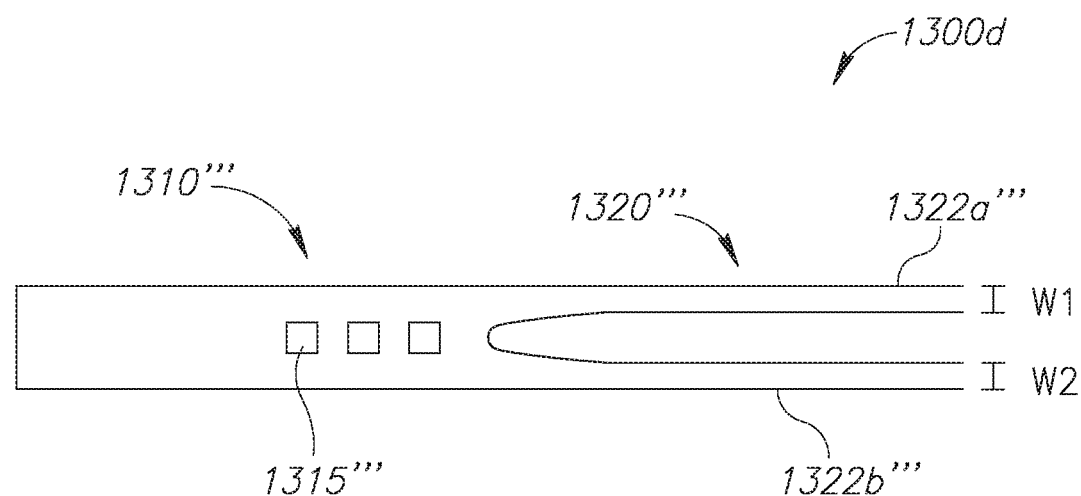
FIG. 11D schematically illustrates a single plate having a first section and a second section, the first section configured to be coiled into a coil positionable within a vascular malformation and the second section forming two strands which, when deployed, are configured to form a secondary structure engaging the parent vessel.

Reference is now made to FIG. 11D, which shows a single strip 1300d having a first section 1310'" and a second section 1320'". First section 1310'" is configured to be twined into the form of a twisted strip and subsequently to be coiled into a coil positionable within a vascular malformation. Second section 1320'" forms two strands 1322a'" and 1322b'", which, when deployed, are configured to form a secondary structure (e.g. a double stranded helix) suitable for engaging an inner wall of an adjacent blood vessel (the parent vessel). First section 1310'" further includes a plurality of windows, illustratively depicted as three windows, such as window 1315'" distributed along a part of first section 1310'" closest to second section 1320'". This serves to ensure that the looping of first section 1310'" is eased, as the loops are getting smaller.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" or "comprising," when used in this specification, specify the presence of stated features, integers, steps, operations, elements, or components, but do not preclude or rule out the presence or addition of one or more other features, integers, steps, operations, elements, components, or groups thereof.

While a number of exemplary aspects and embodiments have been discussed above, those of skill in the art will recognize certain modifications, additions and sub-combinations thereof. It is therefore intended that the following appended claims and claims hereafter introduced be interpreted to include all such modifications, additions and sub-combinations as are within their true spirit and scope.

What we claim is:

1. A non-occlusive device for use with a microcatheter and for treating a vascular malformation, the device comprising:
    a coilable section configured to become coiled into a coil when deployed from the microcatheter within the vascular malformation; wherein said coil is shaped so as to define a sequence of concentric loops; and wherein said coil is configured to bridge a neck of the vascular malformation so as to at least partially cover an orifice of the vascular malformation, when in use;

a docking section configured to be deployed from the microcatheter within the vascular malformation; wherein the docking section is configured to, when in use, perform one or more functions selected from the group consisting of: anchoring the device within the vascular malformation, stabilizing the device within the vascular malformation, assisting with positioning of the device within the vascular malformation, and intertwining detachable coils delivered to the vascular malformation; and an intermediate section, interconnecting said coilable section and said docking section, and comprising a swivel configured to enable the coilable section to revolve without turning the docking section.

2. The device of claim 1, wherein said coilable section and said docking section are formed from a single wire.

3. The device of claim 2, wherein the docking section is configured to be deployed from a distal end of the microcatheter within the vascular malformation, and wherein the docking section is formed of a distal most part of said single wire.

4. The device of claim 2, wherein the coilable section is proximal to said docking section on said single wire.

5. The device of claim 1, wherein the vascular malformation is a wide-neck aneurysm, and wherein the coilable section is configured to be deployed from the microcatheter within the wide-neck aneurysm.

6. The device of claim 1, wherein said coilable section enables controlled positioning of the device within the vascular malformation from a central axis thereof.

7. The device of claim 1, wherein said device is configured such that said coil assumes a form of a bowl when deployed from the microcatheter within the vascular malformation.

8. The device of claim 1, wherein said device is configured such that said coil assumes a form of a flat plate, when deployed from the microcatheter within the vascular malformation.

9. The device of claim 1, wherein said coilable section, said docking section, or said coilable section and said docking station comprise a memory shape alloy.

10. The device of claim 1, wherein said coilable section, said docking section, or said coilable section and said docking station comprise a super elastic alloy.

11. The device of claim 1, wherein said device is configured such that a distal end of said coilable section forms an innermost loop of said coil and a proximal end of said coilable section forms an outermost loop of said coil when said device is deployed from the microcatheter within the vascular malformation.

12. The device of claim 1, wherein said device is configured such that a proximal end of said coilable section forms an innermost loop of said coil and a distal end of said coilable section forms an outermost loop of said coil when said device is deployed from the microcatheter within the vascular malformation.

13. The device of claim 1, wherein said docking section comprises one or more concentric loops.

14. The device of claim 1, wherein said device is configured such that said coil comprises an aperture essentially in a center thereof when said device is deployed from the microcatheter within the vascular malformation.

15. The device of claim 14, wherein said device is configured such that said aperture is sized and shaped to allow passage of a microcatheter delivering embolic material therethrough after said device is deployed from the microcatheter within the vascular malformation.

16. The device of claim 1, wherein said coilable section further comprises a core wire within at least part of said coilable section.

17. The device of claim 16, wherein said docking section is devoid of said core wire.

18. A method for treating a wide-neck aneurysm, the method comprising:

deploying a docking section of a non-occlusive device from a microcatheter within the wide-neck aneurysm such that the docking section performs one or more functions selected from the group consisting of: anchoring the device within the aneurysm, stabilizing the device within the aneurysm, assisting with positioning of the device within the wide-neck aneurysm, and intertwining;

deploying an intermediate section of the non-occlusive device from the microcatheter within the wide-neck aneurysm; and deploying a coilable section of the non-occlusive device from the microcatheter within the wide-neck aneurysm, such that the coilable section becomes coiled into a coil that bridges a neck of the aneurysm so as to at least partially cover an orifice of the aneurysm, the coil shaped so as to define a sequence of concentric loops, wherein said intermediate section interconnects said coilable section and said docking section, and includes a swivel configured to enable the coilable section to revolve without turning the docking section.

19. The method of claim 18, wherein deploying the docking section comprises deploying the docking section such that the docking section anchors the device within the aneurysm.

20. The method of claim 18, further comprising delivering embolic material to the wide-neck aneurysm such that the coilable section of the non-occlusive device prevents protrusion of the embolic material through the neck of the wide-neck aneurysm.

21. The device of claim 1, wherein the docking section is configured to anchor the device within the vascular malformation when in use.

\* \* \* \* \*